(12) United States Patent
Arora et al.

(10) Patent No.: US 7,622,473 B2
(45) Date of Patent: Nov. 24, 2009

(54) 'N-(2-CHLORO-6-METHYLPHENYL)-2-[[(6-[4-(2-HYDROXYETHYL)-1-PIPERAZINYL]-2-METHYL-4-PYRIMIDINYL]AMINO]-5-THIAZOLECARBOXAMIDES METABOLITES

(75) Inventors: Vinod Kumar Arora, Cheshire, CT (US); Lisa Joy Christopher, East Windsor, NJ (US); Donghui Cui, Chalfont, PA (US); Wenying Li, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 481 days.

(21) Appl. No.: 11/376,665

(22) Filed: Mar. 15, 2006

(65) Prior Publication Data

US 2006/0211705 A1    Sep. 21, 2006

Related U.S. Application Data

(60) Provisional application No. 60/661,777, filed on Mar. 15, 2005, provisional application No. 60/728,732, filed on Oct. 20, 2005.

(51) Int. Cl.
*A61K 31/497* (2006.01)
*C07D 403/00* (2006.01)

(52) U.S. Cl. .................................. 514/252.19; 544/295
(58) Field of Classification Search ............. 514/252.19
See application file for complete search history.

(56) References Cited

U.S. PATENT DOCUMENTS

| | | |
|---|---|---|
| 6,596,746 B1 | 7/2003 | Das et al. |
| 2004/0054186 A1 | 3/2004 | Das et al. |
| 2005/0009891 A1 | 1/2005 | Lee |
| 2005/0261305 A1 | 11/2005 | Das et al. |
| 2005/0288303 A1 | 12/2005 | Das et al. |
| 2006/0004067 A1 | 1/2006 | Chen et al. |
| 2006/0069101 A1* | 3/2006 | Kim et al. ............... 514/252.19 |
| 2006/0079563 A1 | 4/2006 | Das et al. |

FOREIGN PATENT DOCUMENTS

| | | | |
|---|---|---|---|
| WO | WO00/62778 | * | 4/2000 |
| WO | WO2006/081172 | * | 3/2006 |

OTHER PUBLICATIONS

Dorwald F. A. Side Reactions in Organic Synthesis, 2005, Wiley: VCH, Weinheim p. IX of Preface.*
http://www.encyclopedia.com/doc/1E1-metabolit.html; last accessed on Aug. 25, 2008.*
Neil P. Shah et al., "Overriding Imatinib Resistance with a Novel ABL Kinase Inhibitor", Science, vol. 305, Jul. 16, 2004, pp. 399-401.
Louis J. Lombardo et al., "Discovery of N-(2-Chloro-6-methylphenyl)-2-(6-(4-(2-hydroxyethyl)piperazin-1-yl)-2-methylpyrimidin-4-ylamino)thiazole-5-carboxamide (BMS-354825), a Dual Src/Abl Kinase Inhibitor with Potent Antitumor Activity in Preclinical Assays", J. Med. Chem., vol. 47, 2004, pp. 6658-6661.

* cited by examiner

*Primary Examiner*—James O Wilson
*Assistant Examiner*—Jeffrey H Murray
(74) *Attorney, Agent, or Firm*—Mary K. VanAtten

(57) ABSTRACT

The present invention is directed to metabolites of 'N-(2-Chloro-6-methylphenyl)-2-[[6-[4-(2-hydroxyethyl)-1-piperazinyl]-2-methyl-4-pyrimidinyl]amino]-5-thiazolecarboxamide, the compound of formula (I), pharmaceutical compositions thereof, and to methods of using the metabolites and the pharmaceutical compositions in the treatment of oncological and immunological disorders.

(I)

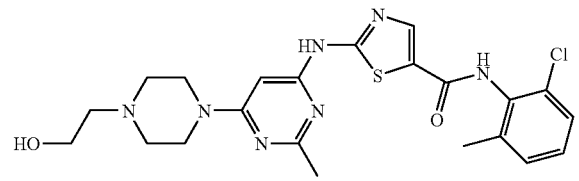

10 Claims, No Drawings

'N-(2-CHLORO-6-METHYLPHENYL)-2-[[(6-[4-(2-HYDROXYETHYL)-1-PIPERAZINYL]-2-METHYL-4-PYRIMIDINYL]AMINO]-5-THIAZOLECARBOXAMIDES METABOLITES

RELATED APPLICATIONS

This application claims priority benefit under Title 35 § 119(e) of U.S. provisional Application Nos. 60/728,732, filed Oct. 20, 2005, and 60/661,777, filed Mar. 15, 2005, the contents of which are herein incorporated by reference.

FIELD OF THE INVENTION

The invention relates to metabolites of 'N-(2-Chloro-6-methylphenyl)-2-[[6-[4-(2-hydroxyethyl)-1-piperazinyl]-2-methyl-4-pyrimidinyl]amino]-5-thiazolecarboxamide, pharmaceutical compositions thereof, and to methods of using the metabolites and the pharmaceutical compositions in the treatment of oncological and immunological disorders

BACKGROUND OF THE INVENTION

The compound of formula (I) 'N-(2-Chloro-6-methylphenyl)-2-[[6-[4-(2-hydroxyethyl)-1-piperazinyl]-2-methyl-4-pyrimidinyl]amino]-5-thiazolecarboxamide, is a protein tyrosine kinase inhibitor, a Src Kinase inhibitor and is useful in the treatment of immunologic and oncological diseases.

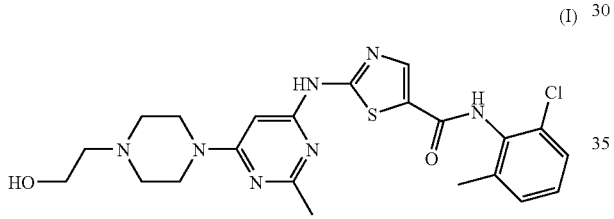
(I)

The compound of formula (I) and its preparation have been previously described in U.S. Pat. No. 6,596,746, issued Jul. 22, 2003.

SUMMARY OF THE INVENTION

The present invention is directed to compounds which are metabolites of the compound of formula (I), pharmaceutical compositions thereof and to methods of treating immunologic and oncological disorders.

DETAILED DESCRIPTION OF EMBODIMENTS OF THE INVENTION

The present invention is directed to compounds which are metabolites of the compound of formula (I)

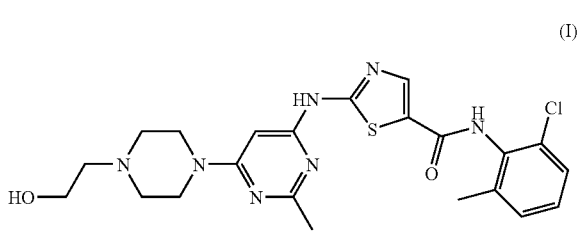
(I)

or pharmaceutically acceptable salt forms thereof.

In another embodiment of the invention, the compounds which are metabolites of the compound of formula (I) are present in substantially pure form.

The substantially pure compounds may be combined with other ingredients to form pharmaceutical compositions thereof.

The compounds which are metabolites of the compound of formula (I) are represented by the compounds of formula (II), (III), (IV), (V), and (VI).

The compounds which are metabolites of the compound of formula (I) are further represented by the compounds described in the Tables and Schemes.

In another embodiment of the invention is directed to a purified compound of formula (II),

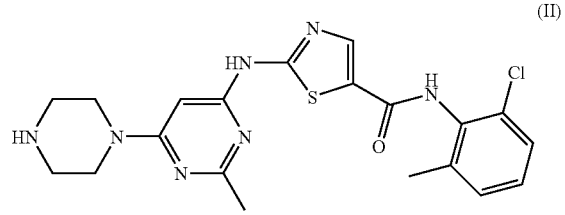
(II)

or pharmaceutically acceptable salt forms thereof.

In another embodiment of the invention is directed to a purified compound of formula (III),

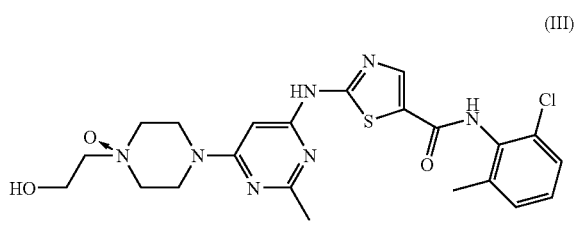
(III)

or pharmaceutically acceptable salt forms thereof.

In another embodiment of the invention is directed to a purified compound of formula (IV),

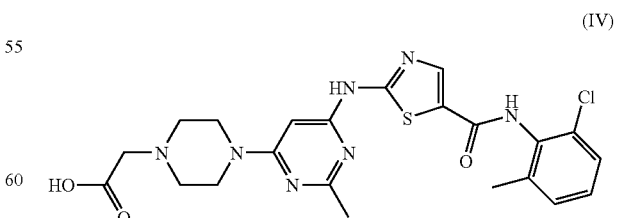
(IV)

or pharmaceutically acceptable salt forms thereof.

In another embodiment of the invention is directed to a purified compound of the following formula (V), (V)

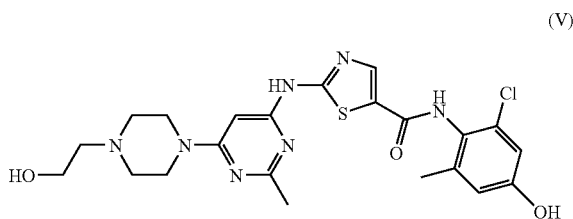

or pharmaceutically acceptable salt forms thereof.

In another embodiment of the invention is directed to a purified compound of the following formula (VI), (VI)

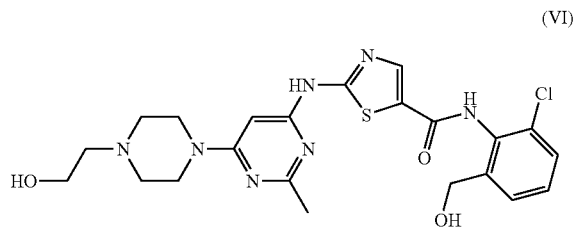

or pharmaceutically acceptable salt forms thereof.

In another embodiment of the invention is directed to a purified metabolite of the compound of formula (I)

(I)

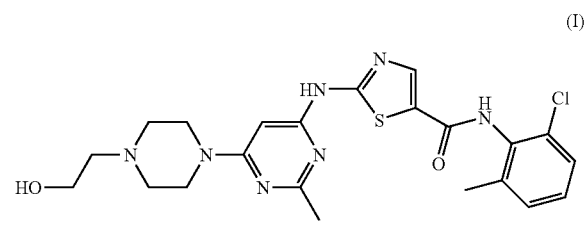

or pharmaceutically acceptable salt form thereof, wherein the purified metabolite is a glucoronide, a sulfate conjugate, an oxidation compound, a dehydrogenated compound, dual cleavage of piperazine compound, a bis-oxygenated compound, a monohydroxylated compound, a sulfate conjugate of monohydroxylated compound, or a taurine conjugate, or combinations of the above described modifications.

In another embodiment of the invention is directed to a purified compound which is a metabolite of the compound of formula (I), wherein the metabolite is a compound having a molecular ion $[M+H]^+$ of m/z 664, loss of 176, and a major MS/MS fragment at m/z 488, and the $MS^3$ fragmentation of 488 having fragments of 427, 401 and 347.

In another embodiment of the invention is directed to a purified compound which is a metabolite of the compound of formula (I), wherein the metabolite is a compound having a molecular ion $[M+H]^+$ of m/z 568, loss of 80, and major MS/MS fragments at m/z 488, 470, 427, and 347.

In another embodiment of the invention is directed to a purified compound which is a metabolite of the compound of formula (I), wherein the metabolite is a compound having $[M+H]^+$ of m/z 462 and major MS/MS fragments at m/z 401, 375, and 321, and the $MS^3$ fragmentation of m/z 401 having fragments of 260 and 232.

In another embodiment of the invention is directed to a purified compound which is a metabolite of the compound of formula (I), wherein the metabolite is a compound having a molecular ion $[M+H]^+$ of m/z 520 and major MS/MS fragments at m/z 502, 401, and 379, and the $MS^3$ fragmentation of m/z 401 having fragments of 260 and 232.

In another embodiment of the invention is directed to a purified compound which is a metabolite of the compound of formula (I), wherein the metabolite is a compound having a molecular ion $[M+H]^+$ of m/z 504 and major MS/MS fragments at m/z 443, 417, and 347, and the $MS^3$ fragmentation of m/z 417 having fragments of 260 and 232.

In another embodiment of the invention is directed to a purified compound which is a metabolite of the compound of formula (I), wherein the metabolite is a compound having a molecular ion $[M+H]^+$ of m/z 584, loss of 80, and a major MS/MS fragment at m/z 504, and the $MS^3$ fragmentation of m/z 504 having fragments of 486, 443, 417, and 347.

In another embodiment of the invention is directed to a purified compound which is a metabolite of the compound of formula (I), wherein the metabolite is a compound having a molecular ion $[M+H]^+$ of m/z 504 and major MS/MS fragments at m/z 486, and 401, and the $MS^3$ fragmentation of m/z 486 having fragments of 401 and 375.

In another embodiment of the invention is directed to a purified compound which is a metabolite of the compound of formula (I), wherein the metabolite is a compound having a molecular ion $[M+H]^+$ of m/z 518 and major MS/MS fragments at m/z 500 and 361, and the $MS^3$ fragmentation of m/z 500 having major fragments of 399 and 361, and the $MS^3$ fragmentation of m/z 361 having a major fragment of 333.

In another embodiment of the invention is directed to a purified compound which is a metabolite of the compound of formula (I), wherein the metabolite is a compound having a molecular ion $[M+H]^+$ of m/z 504 and major MS/MS fragments at m/z 486, 417, and 347, and the $MS^3$ fragmentation of m/z 486 having major fragments of 399 and 347.

In another embodiment of the invention is directed to a purified compound which is a metabolite of the compound of formula (I), wherein the metabolite is a compound having a molecular ion $[M+H]^+$ of m/z 418 and major MS/MS fragments at m/z 401, and 277, and the $MS^3$ fragmentation of m/z 401 having major fragments of 260 and 232.

In another embodiment of the invention is directed to a purified compound which is a metabolite of the compound of formula (I), wherein the metabolite is a compound having a molecular ion $[M+H]^+$ of m/z 609 and major MS/MS fragments at m/z 468, 456, 444, and 401, and the $MS^3$ fragmentation of m/z 468 having major fragments of 440 and 303.

In another embodiment of the invention is directed to a purified compound which is a metabolite of the compound of formula (I), wherein the metabolite is a compound having a molecular ion $[M+H]^+$ of m/z 520, and $MS^2$ fragment ions at m/z 476, 417 and 363.

In another embodiment of the invention is directed to a purified compound which is a metabolite of the compound of formula (I), wherein the metabolite is a compound having a molecular ion $[M+H]^+$ of m/z 518, $MS^2$ of m/z 518 having a major fragment ion at m/z 456, and the m/z 456 ($MS^3$) having fragment ions at m/z 401 and 375.

In another embodiment of the invention is directed to a purified compound which is a metabolite of the compound of formula (I), wherein the metabolite is a compound having a molecular ion $[M+H]^+$ of m/z 486, and $MS^2$ fragment ions at m/z 347, 319, and 263.

In another embodiment of the invention is directed to a purified compound which is a metabolite of the compound of formula (I), wherein the metabolite is a compound having a molecular ion [M+H]$^+$ of m/z 518, and MS$^2$ fragment ions at m/z 417 and 361.

In another embodiment of the invention is directed to a purified compound which is a metabolite of the compound of formula (I), wherein the metabolite is a compound having a molecular ion [M+H]$^+$ of m/z 518, and MS$^2$ fragment ions at m/z 361 and 500.

In another embodiment of the invention is directed to a purified compound which is a metabolite of the compound of formula (I), wherein the metabolite is a compound having a molecular ion [M+H]$^+$ of m/z 460, and MS$^2$ fragment ions at m/z 303 and 275, and 417.

In another embodiment of the invention is directed to a purified compound which is a metabolite of the compound of formula (I), wherein the metabolite is a compound having a molecular ion [M+H]$^+$ of m/z 460, and MS$^2$ fragment ions at m/z 303 and 442.

In another embodiment of the invention is directed to purified compounds which are metabolites of the compound of formula (I), wherein the metabolites are compounds having a molecular ion [M+H]$^+$ of m/z 520, and MS$^2$ fragment ions at m/z 433 and 347, and MS$^3$ of m/z 443 fragment ions at m/z 397 and 260.

In another embodiment of the invention is directed to a purified compound which is a metabolite of the compound of formula (I), wherein the metabolite is a compound having a molecular ion [M+H]$^+$ of m/z 598, and MS$^2$ fragment ions of m/z 518, 417, and 361.

In another embodiment of the invention is directed to a purified compound which is a metabolite of the compound of formula (I), wherein the metabolite is a compound having a molecular ion [M+H]$^+$ of m/z 600, an MS$^2$ fragment ion at m/z 520, and MS$^3$ of m/z 520 having fragment ions at m/z 433 and 347.

In another embodiment of the invention is directed to a purified compound which is a metabolite of the compound of formula (I), wherein the metabolite is a compound having a molecular ion [M+H]$^+$ of m/z 534, and MS$^2$ fragment ions of m/z 534 at m/z 472, 403, 377, and 333.

In another embodiment of the invention is directed to purified compounds which are metabolites of the compound of formula (I), wherein the metabolites are compounds having a molecular ion [M+H]$^+$ of m/z 662, a major MS$^2$ fragment ion at 486, and MS$^3$ of 486 fragment ions of 399, 347, and 263.

In another embodiment of the invention is directed to a purified compound which is a metabolite of the compound of formula (I), wherein the metabolite is a compound having a molecular ion [M+H]$^+$ of m/z 694, a major MS$^2$ fragment ion at m/z 518, and further fragmentation of m/z 518 having ions at m/z 417 and 361.

In another embodiment of the invention is directed to purified compounds which are metabolites of the compound of formula (I), wherein the metabolites are compounds having a molecular ion [M+H]$^+$ of m/z 680, a major MS$^2$ fragment ion at m/z 504, and MS$^3$ fragment ions of m/z 504 at m/z 417 and 347.

In another embodiment, the invention is directed to purified compound which is a metabolites of the compound of formula (I), wherein the metabolite is a compound having a molecular ion of m/z 664 under positive full MS scans and MS$^2$ spectra containing a neutral 176 Da loss and fragment ions at m/z 488 and 401.

In another embodiment of the invention is directed to purified compounds which are metabolites of the compound of formula (I), wherein the metabolites are compounds having a molecular ion [M+H]$^+$ of m/z 518, MS$^2$ fragment ions at m/z 417 and 361.

In another embodiment of the invention is directed to purified compound which is a metabolites of the compound of formula (I), wherein the metabolite is a compound having a molecular ion [M+H]$^+$ of m/z 534 and having major fragment ions of m/z 534 of ions at m/z 472, 403, 377, and 333.

In another embodiment of the invention is directed to purified compound which is a metabolites of the compound of formula (I), wherein the metabolites are compounds having a molecular ion [M+H]$^+$ of m/z 662, MS$^2$ spectra containing a neutral 176 Da, and fragment ions at m/z 486 and 399 and m/z 347.

In another embodiment of the invention is directed to purified compound which is a metabolites of the compound of formula (I), wherein the metabolite is a compound having a molecular ion [M+H]$^+$ of m/z 694, MS$^2$ spectra of m/z 694 containing a major fragment ion at m/z 518, and a neutral 176 Da loss from m/z 694, and further fragmentations of m/z 518 including ions at m/z 417 and 361.

In another embodiment of the invention is directed to purified compounds which are metabolites of the compound of formula (I), wherein the metabolites are compounds having a molecular ion [M+H]$^+$ of m/z 680, MS$^3$ spectra of m/z 680 containing a major fragment ion at m/z 504 (neutral 176 Da loss), MS$^3$ spectra of m/z 504 containing ions at m/z 417 and 347.

The metabolites of the compound of formula (I) are further represented by the compounds described in the Tables and Schemes.

In another embodiment, there is provided a pharmaceutical composition, comprising a pharmaceutically acceptable carrier and a therapeutically effective amount of a compound of the present invention.

In another embodiment, there is provided a method for treating oncological or immunological disorders, comprising administering to a patient in need thereof a therapeutically effective amount of a compound of the present invention.

In another embodiment, there is provided the use of the compounds of the present invention in therapy.

In another embodiment, there is provided the use of the compounds of the present invention in the preparation of a medicament for the treatment of oncological or immunological disorders.

The invention may be embodied in other specific forms without departing from the spirit or essential attributes thereof. This invention also encompasses all combinations of preferred aspects and examples of the invention noted herein. It is understood that any and all embodiments of the present invention may be taken in conjunction with any other embodiment to describe additional even more preferred embodiments of the present invention. Furthermore, any elements of an embodiment are meant to be combined with any and all other elements from any of the embodiments to describe additional embodiments.

Definitions

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds. The structures of the metabolites may be shown with a substituent bonded to a portion of the molecule. This is meant to indicate that that substituent may be present at any location on that portion of the molecule and the exact location is not definitely known.

The compounds of the present invention, which are metabolites of the compound of formula I, form salts which are also within the scope of this invention. Reference to a compound herein is understood to include reference to salts thereof, unless otherwise indicated. The term "salt(s)", as employed herein, denotes acidic and/or basic salts formed with inorganic and/or organic acids and bases. In addition, when compounds of the present invention contain both a basic moiety, such as, but not limited to an amine or a pyridine ring, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds may be formed, for example, by reacting a compound of the present invention with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines [formed with N,N-bis(dehydro-abietyl)ethylenediamine], N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Metabolites of the compound of formula I, and salts thereof, may exist in their tautomeric form, in which hydrogen atoms are transposed to other parts of the molecules and the chemical bonds between the atoms of the molecules are consequently rearranged. It should be understood that all tautomeric forms, insofar as they may exist, are included within the invention. Additionally, inventive compounds may have trans and cis isomers and may contain one or more chiral centers, therefore existing in enantiomeric and diastereomeric forms. The invention includes all such isomers, as well as mixtures of cis and trans isomers, mixtures of diastereomers and racemic mixtures of enantiomers (optical isomers). When no specific mention is made of the configuration (cis, trans or R or S) of a compound (or of an asymmetric carbon), then any one of the isomers or a mixture of more than one isomer is intended. The processes for preparation can use racemates, enantiomers, or diastereomers as starting materials. When enantiomeric or diastereomeric products are prepared, they can be separated by conventional methods, for example, by chromatographic or fractional crystallization. The inventive compounds may be in the free or hydrate form.

In addition, metabolites of the compound of formula I may have prodrug forms. Any compound that will be converted in vivo to provide the bioactive agent (i.e., a compound of formula I) is a prodrug within the scope and spirit of the invention.

For example, pro-drug compounds of metabolites of formula I may be carboxylate ester moieties. A carboxylate ester may be conveniently formed by esterifying any of the carboxylic acid functionalities found on the disclosed ring structure(s). Various forms of prodrugs are well known in the art. For examples of such prodrug derivatives, see:
  a) Design of Prodrugs, edited by H. Bundgaard, (Elsevier, 1985), and Methods in Enzymology, Vol. 112, at pp. 309-396, edited by K. Widder, et. al. (Academic Press, 1985);
  b) A Textbook of Drug Design and Development, edited by Krosgaard-Larsen and H. Bundgaard, Chapter 5, "Design and Application of Prodrugs," by H. Bundgaard, at pp. 113-191 (1991);
  c) H. Bundgaard, Advanced Drug Delivery Reviews, Vol. 8, pp. 1-38 (1992);
  d) H. Bundgaard, et al., Journal of Pharmaceutical Sciences, Vol. 77, p. 285 (1988); and
  e) N. Kakeya, et. al., Chem Phar Bull, Vol. 32, p. 692 (1984).

It should further be understood that solvates (e.g., hydrates) of the compounds of formula I are also with the scope of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Substantially pure" as used herein is intended to include a compound having a purity greater than 90 weight percent, including 90, 91, 92, 93, 94, 95, 96, 97, 98, 99, and 100 percent.

As one example, a metabolite of the compound of the formula (I) can be substantially pure in having a purity greater than 90 percent (by weight), where the remaining less than 10 percent of material comprises other metabolite(s) of the compound of the formula (I), the compound of formula (I), and/or reaction and/or processing impurities arising from its preparation.

A metabolite of the compound of the formula (I) in substantially pure form may be employed in pharmaceutical compositions to which other desired components are added, for example, excipients, carriers, or active chemical entities of different molecular structure.

"Therapeutically effective amount" is intended to include an amount of a compound of the present invention alone or an amount of the combination of compounds claimed or an amount of a compound of the present invention in combination with other active ingredients effective to inhibit protein tyrosine kinase activity, such as but not limited to Src kinase activity, or effective to treat or prevent oncological or immunological disorders.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Metabolite Isolation

The metabolites of the compound of formula (I) were isolated from urine, bile, and plasma samples utilizing the following procedures.

Two groups of two BDC (bile duct cannulated) male Sprague-Dawley rats each were dosed with the compound of formula (Ia) ([$^{14}$C] of the compound of formula (I), see below) (10 mg/kg, 60 µCi/kg) either by intravenous (IV) or oral (PO) routes of administration. Two additional groups of six intact male Sprague-Dawley rats each were also dosed with the compound of formula (Ia) (10 mg/kg, 60 µCi/kg) by IV or PO routes of administration. Dosing solutions of (Ia) were prepared at a concentration of 2.0 mg/mL, 12.3 µCi/mL in 50 mM sodium acetate buffer (pH 4.0), one day prior to administration and were kept at room temperature until the time of dosing. After dosing, bile was collected from the BDC rats at 0-6 and 6-12 h intervals (groups 1 and 3). During the period of sample collection (0-12 h), bile was replenished by infusing control bile, collected in the days prior to dose administration, at a rate of 1 mL/hr. Urine was collected from the bile duct cannulated rats over a 0-12 h interval (groups 1 and 3). The volume of bile and urine from each animal at each interval was recorded. EDTA plasma was prepared from blood samples that had been collected via cardiac puncture from intact rats at 1, 4, and 8 h (groups 2 and 4). No feces were collected.

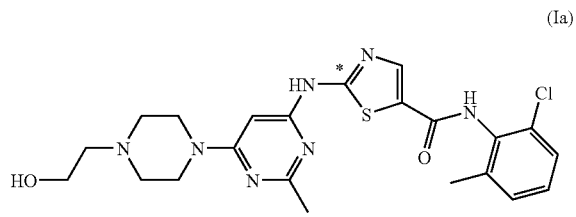

(Ia)

(wherein * denotes the location of the [$^{14}$C] label)

Representative pooled bile and urine samples were prepared by combining a constant volume percentage from each sample excreted during the 0-12 h interval for each animal within a treatment group (groups 1 and 3, intravenous and oral drug administration, respectively). Representative pooled plasma samples were prepared by combining equal volumes of the two samples collected at each time point (1, 4, and 8 h) for each treatment (IV, or PO). Portions of the pooled bile and urine samples (50 µL each) and pooled plasma samples (100 µL each) were counted on the LSC for 10 min to determine the initial radioactive concentration.

Aliquots of pooled rat bile samples, 200 µL, were diluted with 1 mL of water and loaded onto Waters Oasis™ HLB solid-phase extraction (SPE) cartridges (1 cc) that had been pre-conditioned first with methanol and then water. The extracted components were eluted from the SPE cartridges with 2 mL of 0.1% formic acid in methanol. Radioactivity in the eluate was measured by LSC. Solvent was evaporated under a stream of nitrogen gas at room temperature. The dried residues were reconstituted in 300 µL of 50:50 (vol/vol) acetonitrile/water. The samples were then vortexed, sonicated for 5 min, and centrifuged at 13,000 rpm for 10 min at 5° C. in a Heraeus Biofuge Fresco refrigerated centrifuge (Heraeus Sepatech GmbH, Germany). The supernatants were transferred to autosampler vials and injected onto the HPLC for biotransformation profiling.

Aliquots of pooled rat urine, 200 µL, were centrifuged at 13,000 rpm for 10 min, at 5° C. in a Heraeus Biofuge Fresco centrifuge. The supernatants were transferred to autosampler vials and injected onto the HPLC system for biotransformation profiling.

Pooled rat plasma samples (1.4-2.0 mL) were extracted two times with 5 mL of 50:50 (vol/vol) methanol/acetonitrile and a third time with 3 mL of 50:50 (vol/vol) methanol/acetonitrile. After addition of organic solvent in each extraction step, samples were vortexed to re-suspend the solid material and then sonicated for 5 min. The extracted samples were centrifuged at 3,000 rpm for 10 min at 5° C. in a Eppendorf model 5810R centrifuge, and the supernatants from each centrifugation step were combined. The combined supernatants were evaporated to dryness at room temperature under a stream of nitrogen gas. The dried residues were reconstituted in 200 µL acetonitrile/water (approximate ratio 35:65 vol/vol). The samples were then centrifuged at 13,000 rpm for 10 min, at 5° C. in a Heraeus Biofuge Fresco centrifuge. The supernatants were transferred to autosampler vials and injected onto the HPLC system for biotransformation profiling.

HPLC analyses were performed on a Shimadzu Class VP® system equipped with a system controller (model SCL-10A), two pumps (model LC-10AD), an autoinjector (SIL-10AD) and a photodiode array detector (SPD-M10A). Samples for biotransformation profiling (bile, urine and plasma) were injected onto a Waters YMC™-ODS-AQ column (3.0 mm×150 mm, 3 micron particle size) equipped with a guard column. The column temperature was maintained at 35° C. with an Eppendorf TC-45 controller and CH-30 column heater system. The column eluate was monitored at a wavelength of 323 nm. Separation of sample components was achieved with a mobile phase with consisting of two solvents: A) 0.1% trifluoroacetic acid in water and B) 0.1% trifluoroacetic acid in acetonitrile. The mobile phase flow rate was 0.4 mL/min. The gradient program used to elute the samples from the column is described in the following table:

| Time (min) | Solvent A(%) | Solvent B (%) |
|---|---|---|
| 0.02 | 95 | 5 |
| 1 | 95 | 5 |
| 5 | 85 | 15 |
| 52 | 68 | 32 |
| 55 | 5 | 95 |
| 60 | 5 | 95 |
| 61 | 95 | 5 |
| 70 | 95 | 5 |

The retention times of reference standards were confirmed by their UV absorbance and peaks were identified as drug-related by their UV spectra with the diode-array detector. For quantification of radioactivity, the HPLC eluate was collected in 0.25-min intervals on Deepwell LumaPlate™-96-well plates with a Gilson Model FC 204 fraction collector (Gilson, Middleton, Wis.). Fractions of column eluate were evaporated to dryness either in a solvent fume hood overnight or on a Savant Speed-Vac (Savant Instruments Inc., Holbrook, N.Y.) and were counted for radioactivity with a Packard Top Count® microplate scintillation analyzer (Packard Biosciences, Downers Grove, Ill.).

LC/MS/MS and LC/MS$^3$ analyses were performed on pooled bile (0-12 h), urine (0-12 h) and plasma (1, 4, and 8 h) samples prepared as described above. Mass spectrometry was performed using either a Finnigan LCQ or a Finnigan LCQ Deca XP ion trap mass spectrometer. A Waters YMC™ ODS-AQ column (3.0×150 mm, 3 micron particle size) equipped with a guard column was used for separation of drug-related components. The HPLC solvent system and mobile phase gradient used are described above. The flow rate was 0.40 mL/min.

Mass spectral analysis of all standards and metabolites was performed with an ESI probe operating in the positive ion mode. The eluate from the HPLC was directed into the mass spectrometers through a valve set to divert the flow from 0-5 min. From 5 min to 65 min, the HPLC eluate was directed into the mass spectrometer. The flow was again diverted from the mass spectrometer over the 65-70 min interval. The capillary temperature used for analysis was 275° C. on the Finnigan LCQ and 300° C. on the LCQ Dexa XP. The nitrogen gas flow, spray current, and voltages were adjusted as needed to provide maximum sensitivity.

The identities of all metabolites were confirmed by LC/MS/MS or LC/MS$^3$ analysis. A summary of the major ions observed in the mass-spectra and proposed structures of the metabolites are presented below in Tables 4 and 5. Comparison of mass-spectral fragmentation patterns and retention times to those of synthetic standards the compound of formula (I), the compound of formula (II), the compound of formula (III), and the compound of formula (IV) provided additional verification for the identity of the parent, M4, M6, and M5, respectively.

The compound of formula (I) reference standard showed a molecular ion [M+H]$^+$ of m/z 488, and MS/MS fragments at 427, 401 and 347. The MS$^3$ fragmentation of m/z 401 produced fragments of 260 and 232. A similar mass-spectral fragmentation pattern was observed for the parent compound in in vivo samples.

The compound of formula (II) reference standard showed a molecular ion [M+H]$^+$ of m/z 444 and major MS/MS fragments at m/z 401, 375, 303, and 275. The MS$^3$ fragmentation of m/z 401 produced fragments of 260 and 232. M4, an N-dealkylated metabolite of the compound of formula (I) had the same fragmentation pattern as the synthetic standard of formula (II).

The compound of formula (II) reference standard showed a molecular ion [M+H]$^+$ of m/z 504 and major MS/MS fragments at m/z 460, 427, 401, 402, 387, and 375. The MS$^3$ fragmentation of m/z 460 produced fragments of 442, 401, 387, 375, and 319. M5, an N-oxide metabolite of the compound of formula (I), had the same fragmentation pattern as the synthetic standard of formula (III).

The compound of formula (IV) reference standard showed a molecular ion [M+H]$^+$ of m/z 502 and major MS/MS fragments at m/z 401, 361, and 333. The MS$^3$ fragmentation of m/z 361 produced a major fragment of 333. M6, a metabolite of the compound of formula (I) in which the ethanol group has been oxidized to a carboxylic acid, had the same fragmentation pattern as the synthetic standard. Additional MS$^3$ fragmentation of m/z 401 produced major fragments of 260 and 232 of formula (IV).

The metabolite M8 showed a molecular ion [M+H]$^+$ of m/z 664, loss of 176 (characteristic of a glucuronide) and a major MS/MS fragment at m/z 488. The MS$^3$ fragmentation of m/z 488 produced a fragmentation pattern similar to that of the parent molecule. These data support the conclusion that M8 is a glucuronide conjugate of the compound of formula (I). A glucoronide conjugate is a glucuronic acid derivative of the compound of formula (I).

The metabolite M13 showed a molecular ion [M+H]$^+$ of m/z 568, loss of 80 (characteristic of a sulfate conjugate) and major MS/MS fragments at m/z 488, 470, 427, and 347. These data support the conclusion that M13 is a sulfate conjugate of the compound of formula (I).

The metabolite M14 showed a molecular ion [M+H]$^+$ of m/z 462 and major MS/MS fragments at m/z 401, 375, and 321. The MS$^3$ fragmentation of m/z 401 produced fragments of 260 and 232, similar to the MS$^3$ fragmentation of the parent molecule. These data support the conclusion that M14 is a metabolite of the compound of formula (I) having the proposed structure shown in Table 5.

The metabolite M15 showed a molecular ion [M+H]$^+$ of m/z 520 and major MS/MS fragments at m/z 502, 401, and 379. The MS$^3$ fragmentation of m/z 401 produced fragments of 260 and 232, similar to the MS$^3$ fragmentation of the parent molecule. These data support the conclusion that M 15 is a bis-oxygenated metabolite of the compound of formula (I) with the site of both additions on the N-hydroxyethyl piperazine group.

The metabolite M20 showed a molecular ion [M+H]$^+$ of m/z 504 and major MS/MS fragments at m/z 443, 417, and 347. The MS$^3$ fragmentation of m/z 417 produced fragments of 260 and 232. These data suggest that M20 is a monohydroxylated metabolite of the compound of formula (I), with the site of oxidation on the phenyl ring.

The metabolite M21 showed a molecular ion [M+H]$^+$ of m/z 584, loss of 80 (characteristic of a sulfate conjugate) and a major MS/MS fragment at m/z 504. The MS$^3$ fragmentation of m/z 504 produced fragments of 486, 443, 417, and 347. These data support the conclusion that M21 is sulfate conjugate of monohydroxylated compound of formula (I). The MS$^3$ data localize the site of oxidation to the phenyl ring.

The metabolite M22 showed a molecular ion [M+H]$^+$ of m/z 504 and major MS/MS fragments at m/z 486, and 401. The MS$^3$ fragmentation of m/z 486 produced fragments of 401 and 375. These data support the conclusion that M22 is a monohydroxylated metabolite of the compound of formula (I), with the site of oxidation on the N-hydroxyethyl piperazine group.

The metabolite M23 showed a molecular ion [M+H]$^+$ of m/z 518 and major MS/MS fragments at m/z 500 and 361, and the MS$^3$ fragmentation of m/z 500 produced major fragments of 399 and 361. In addition, MS$^3$ fragmentation of m/z 361 produced a major fragment of 333, similar to the MS$^3$ fragmentation pattern for the compound of formula (IV). These data suggest that M23 is a monohydroxylated metabolite of M6, with the site of hydroxylation on the phenyl ring.

The metabolite M24 showed a molecular ion [M+H]$^+$ of m/z 504 and major MS/MS fragments at m/z 486, 417, and 347. The MS$^3$ fragmentation of m/z 486 produced major fragments of 399 and 347. These data suggest that M24 is a monohydroxylated metabolite of the compound of formula (I), with the site of oxidation on the phenyl ring.

The metabolite M25 showed a molecular ion [M+H]$^+$ of m/z 418 and major MS/MS fragments at m/z 401, and 277.

The MS³ fragmentation of m/z 401 produced major fragments of 260 and 232, similar to the MS³ fragmentation pattern observed for M4 and the parent molecule. These data are consistent with the conclusion that M25 is an N-dealkylated metabolite of M14.

The metabolite M26 showed a molecular ion [M+H]⁺ of m/z 609 and major MS/MS fragments at m/z 468, 456, 444, and 401. The MS³ fragmentation of m/z 468 produced major fragments of 440 and 303. These data support the conclusion that M26 is a taurine conjugate of M6. A taurine conjugate is a taurine derivative of the carboxylic acid metabolite (IV).

TABLE 1

Profiles of pooled rat bile collected from 0-12 h after intravenous or oral administration of (Ia) ([¹⁴C] compound of formula (I) (10 mg/kg, 60 µCi/kg))

| Metabolite | [M + H]⁺ | Retention Time Range$^a$ |
|---|---|---|
| M21 | 584 | 17-18 min |
| M23 | 518 | 25-26.5 min |
| M24 | 504 | 26.5-28 min |
| M15 | 520 | 30.5-32.5 min |
| M14 | 462 | 32.5-33 min |
| M26 | 609 | 33-34 min |
| M22 | 504 | 34-35 min |
| M8 | 664 | 35-37 min |
| M4 (II)$^b$ | 444 | 37-40 min |
| M6 (IV)$^b$ | 502 | |
| (I) | 488 | 39-43 min |
| M5 (III) | 504 | 43-46 min |

$^a$Approximate retention times of peaks from HPLC biotransformation profiles; some variation in retention times were observed between injections, most likely due to a sample matrix effect.
$^b$The compound of formula (II) (M4) and the compound of formula (IV) (M6) co-eluted in the HPLC.

TABLE 2

Profiles of pooled rat urine collected 0-12 h after intravenous or oral administration of (Ia) ([¹⁴C] the compound of formula (I) (10 mg/kg, 60 µCi/kg)

| Metabolite | [M + H]⁺ | Retention Time Range$^a$ |
|---|---|---|
| M20 | 504 | 17-18 min |
| M24 | 504 | 25-27 min |
| M25 | 418 | 32-32.5 min |
| M14 | 462 | 32.5-33 min |
| M8 | 664 | 34-35 min |
| M4 (II)$^b$ | 444 | 37-38.5 min |
| M6 (IV)$^b$ | 502 | |
| (I) | 488 | 38.5-39.5 min |
| M5 (III) | 504 | 43-45 min |

$^a$Approximate retention times of peaks form HPLC biotransformation profiles; minor variation in retention times were observed between injections.
$^b$The compound of formula (II) (M4) and The compound of formula (IV) (M6) co-eluted in the HPLC.

TABLE 3

Profiles of pooled rat plasma samples at 1, 4, and 8 h after intravenous or oral administration of (Ia) ([¹⁴C] of the compound of formula (I) (10 mg/kg, 60 µCi/kg))

| Metabolite | [M + H]⁺ | Retention Time Range$^a$ |
|---|---|---|
| M24 | 504 | 25.5-27 min |
| M13 | 568 | 31-32.5 min |
| M14 | 462 | 32.5-33.5 min |

TABLE 3-continued

Profiles of pooled rat plasma samples at 1, 4, and 8 h after intravenous or oral administration of (Ia) ([¹⁴C] of the compound of formula (I) (10 mg/kg, 60 µCi/kg))

| Metabolite | [M + H]⁺ | Retention Time Range$^a$ |
|---|---|---|
| M22$^b$ | 504 | 34-36 min |
| M8$^b$ | 664 | |
| M4 (II)$^c$ | 444 | 36.5-37.8 min |
| M6 (IV)$^c$ | 502 | |
| P (I) | 488 | 38-39 min |
| M5 (III) | 504 | 42.5-45 min |

$^a$Approximate retention times of peaks form HPLC biotransformation profiles; minor variations in retention time were observed between injections.
$^b$Metabolites M22 and M8 co-eluted in the HPLC.
$^c$The compound of formula (II) (M4) and the compound of formula (IV) (M6) co-eluted in the HPLC.

TABLE 4

LC/MS/MS characterizations of the compound of formula (I) and its metabolites

| Identity | Matrix and Route of drug administration | MS | MS² | MS³ |
|---|---|---|---|---|
| P (I) | Bile: IV, PO<br>Urine: IV, PO<br>Plasma: IV, PO | 488 | MS² of 488: 427, 401, 347 | MS³ of 401: 260, 232 |
| M4 (II) | Bile: IV, PO<br>Urine: IV, PO<br>Plasma: IV, PO | 444 | MS² of 444: 401, 375, 303, 275 | MS³ of 401: 260, 232 |
| M5 (III) | Bile: IV, PO<br>Urine: IV, PO<br>Plasma: IV, PO | 504 | MS² of 504: 460, 427, 401, 402, 387, 375 | MS³ of 460: 442, 401, 387, 375, 319 |
| M6 (IV) | Bile: IV, PO<br>Urine: IV, PO<br>Plasma: IV, PO | 502 | MS² of 502: 401, 361, 333 | MS³ of 361: 333<br>MS³ of 401: 260, 232 |
| M8 | Bile: IV, PO<br>Urine: IV, PO<br>Plasma: IV, PO | 664 | MS² of 664: 488 | MS³ of 488: 427, 401, 347 |
| M13 | Plasma: IV, PO | 568 | MS² of 568: 488, 470, 427, 347 | ND$^a$ |
| M14 | Bile: IV, PO<br>Urine: IV, PO<br>Plasma: IV, PO | 462 | MS² of 462: 401, 375, 321 | MS³ of 401: 260, 232 |
| M15 | Bile: IV, PO | 520 | MS² of 520: 502, 401, 379 | MS³ of 401: 260, 232 |
| M20 (V) | Urine: IV, PO | 504 | MS² of 504: 443, 417, 347 | MS³ of 417: 260, 232 |
| M21 | Bile: IV, PO | 584 | MS² of 584: 504 | MS³ of 504: 486, 443, 417, 347 |
| M22 | Bile: IV, PO<br>Plasma: IV, PO | 504 | MS² of 504: 486, 401 | MS³ of 486: 401, 375 |

TABLE 4-continued

LC/MS/MS characterizations of the compound of formula (I) and its metabolites

| Identity | Matrix and Route of drug administration | Positive ion ESI Relevant ions m/z | | |
|---|---|---|---|---|
| | | MS | MS² | MS³ |
| M23 | Bile: IV, PO | 518 | MS² of 518: 500, 361 | MS³ of 500: 399, 361 MS³ of 361: 333 |
| M24 (VI) | Bile: IV, PO Urine: IV, PO Plasma: IV, PO | 504 | MS² of 504: 486, 417, 347 | MS³ of 486: 399, 347 |
| M25 | Urine: IV, PO | 418 | MS² of 418: 401, 277 | MS³ of 401: 260, 232 |
| M26 | Bile: IV, PO | 609 | MS² of 609: 468, 456, 444, 401 | MS³ of 468: 440, 303 |

*ND = not determined

TABLE 5

Structures of the compound of formula (I) and proposed structures of its metabolites

| Identity | Structure |
|---|---|
| (I) | 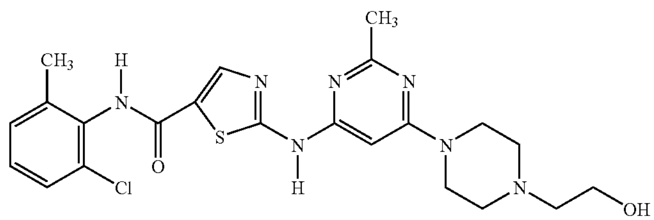 |
| M4 (II) | 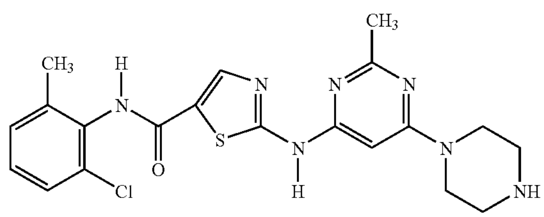 |
| M5 (III) | 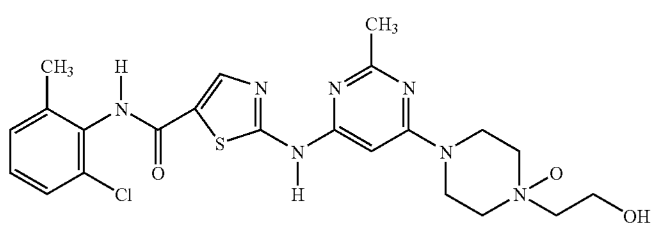 |
| M6 (IV) | 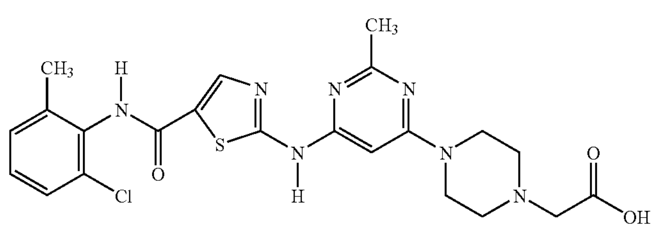 |

TABLE 5-continued
Structures of the compound of formula (I) and proposed structures of its metabolites
| Identity | Structure |
|---|---|
| M8 | 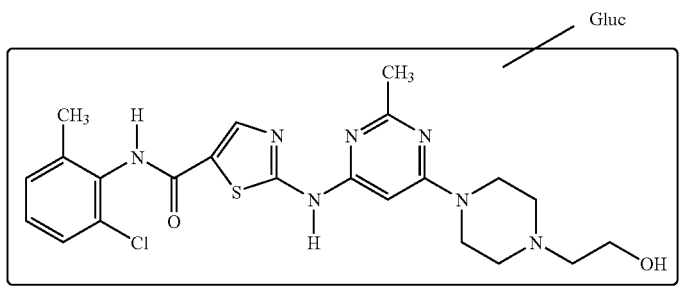 |
| M13* | 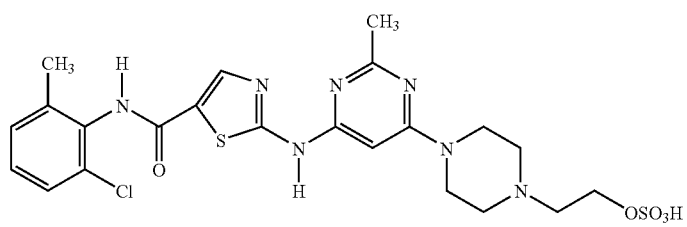 |
| M14 | 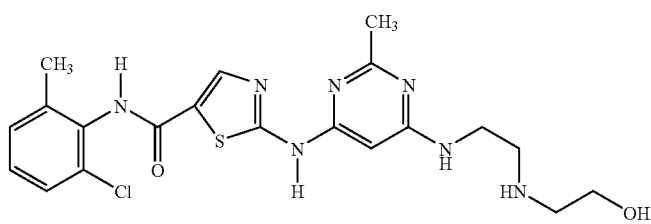 |
| M15 | 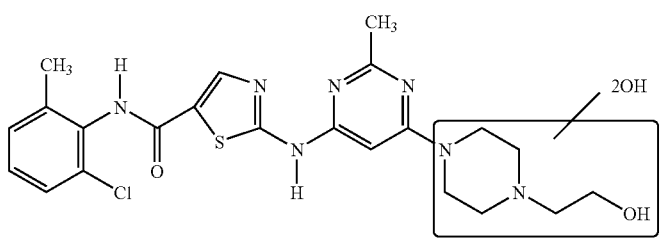 |
| M20* (V) | 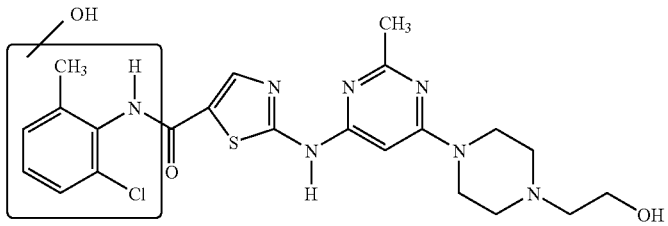 |

TABLE 5-continued
Structures of the compound of formula (I) and proposed structures of its metabolites
| Identity | Structure |
|---|---|
| M21 | 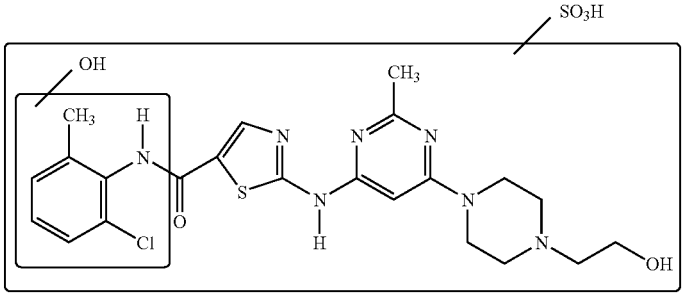 |
| M22 | 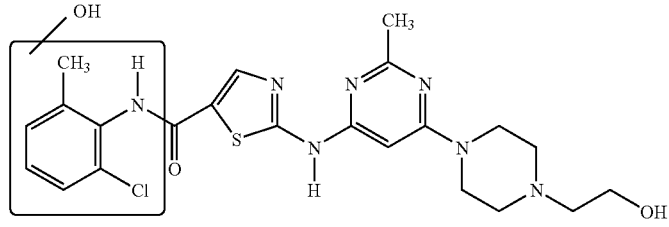 |
| M23 | 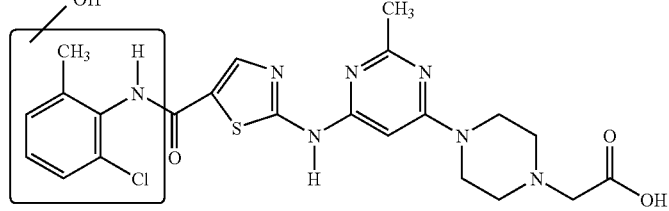 |
| M24* (VI) | 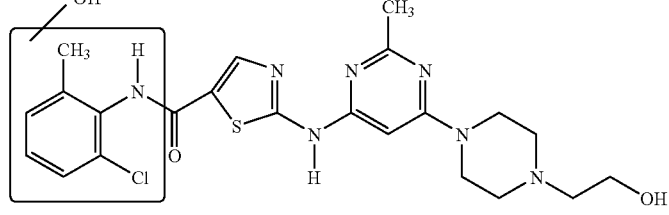 |
| M25 | 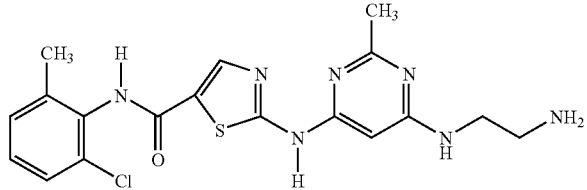 |
| M26 | 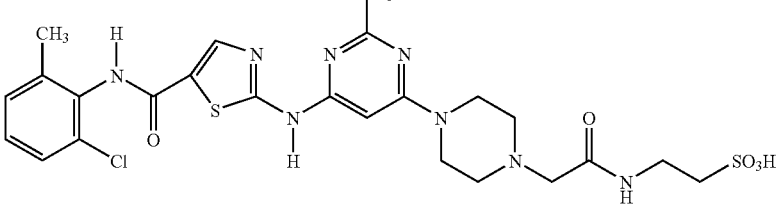 |
*The structures shown for M13, M20 and M24 are as determined from the above described experiments. These structures may be described differently and/or more fully, elsewhere but are consistent with this interpretation.

Metabolites of the compound of formula (I) have also been identified using the methods described below. These metabolites have been analyzed and detected using different method of analysis than those that were described above. Therefore, some of the oxidative metabolites could not be reconciled with the metabolites described above using a method of analysis different from the one used in this account.

The in vitro metabolism of the compound of formula (I) was investigated in liver microsomes and hepatocytes obtained from mouse (CD-1), rat (Sprague-Dawley), dog (Beagle), monkey (Cynomolgus) and human by LC/UV/MS$^n$, see below.

Compound of formula I (10 μM) was incubated with pooled liver microsomes from mouse, rat, dog, monkey and human. Mouse, rat and monkey liver microsomes were obtained from Xenotech, each at a protein concentration of 20 mg/mL. Dog liver microsomes was obtained from In Vitro Technologies with a protein concentration of 20 mg/mL. Human liver microsomes was obtained from Gentest Co. with a protein concentration of 20 mg/mL and CYP concentration of 0.55 nmol/mg.

For each species, the incubation was performed at 37° C. using: 0.1 M potassium phosphate buffer (pH 7.4) containing an NADPH-generating system (0.5 mg/mL glucose-6-phosphate, 0.6 units/mL glucose-6-phosphate dehydrogenase and 0.4 mg/mL of NADPH), 0.91 mg/mL of liver microsomal protein, and 10 μM of compound of formula I. After a 5 minute pre-incubation at 37° C., the reaction was initiated by the addition of compound of formula I and the NADPH-generating system. An aliquot of 200 μl was taken at 0, 15 and 30 minutes and each added immediately to 400 μl of ice-cold acetonitrile to terminate the reaction. The samples were vortexed and centrifuged at 10,000 g for 5 min. All samples were then analyzed by LC/UV/MS/MS.

Compound of formula 1 (30 μM) was incubated with the hepatocytes isolated from mouse (CD-1), rat (Sprague-Dawley), dog (beagle), monkey (cynomolgus) and human. Mouse and rat hepatocytes were prepared freshly as cell suspensions based on a literature protocol (Berry M N, Edwards A M, Barritt G J. Isolated hepatocytes preparation, properties and applications in Laboratory techniques in biochemistry and molecular biology, Elsevier, Amsterdam, 1991). The freshly isolated rat and mouse hepatocytes were subjected to Percoll purification by centrifuging a mixture of cell suspension (12.5 mL) and Percoll solution (12.5 mL) at 50×g for 5 min at 4° C. After a further wash in suspension buffer, the cells were resuspended in the incubation buffer. Fresh dog and monkey hepatocytes were purchased from CEDRA corporation (Austin, Tex.). Cryopreserved human hepatocytes were obtained from In Vitro Technologies (Baltimore, Md., Lot No. 109). The incubations with mouse, rat, dog and monkey hepatocytes were performed with cells from one donor, whereas the incubations with the cryopreserved human hepatocytes were performed with pools from three different donors. Routine viabilities, determined by trypan blue exclusion, of the fresh hepatocytes were >75% and of the cryopreserved hepatocytes were >60%.

For each species the incubation was performed at 37° C., and aliquots of samples (0.2 mL) were taken at 0, 120 min, and the reactions were terminated by adding an equal volume of acetonitrile. The compound was added as a solution in an organic mixture such that the final concentration of DMSO and acetonitrile were 0.015 and 0.085% respectively. The incubations (n=2) were performed at a cell density of 0.67× 106 cells/mL in Krebs-Hensleit buffer fortified with glucose, in an incubator at 37° C., 95% humidity, in an environment of 5% $CO_2$. Samples were stored at −20° C. until analysis.

The in vivo metabolism of compound of formula I was investigated in bile duct cannulated rats (n=2), following a single dose of 10 mg/kg either intravenously (IV) as a 10 minute infusion or orally by gavage. The vehicle used was 50 mM sodium acetate buffer, pH 4.6. The rats were fasted overnight and for the duration of the study. Urine and bile were collected over a 9 hour period. The gastrointestinal tract (GIT) and feces were collected at the end of the 9 hour study period. GIT and feces were homogenized with 3 volumes of water and 3 volumes of acetonitrile per volume of GIT/feces. Blood samples were collected at 15, 30 minutes, 1, 2, 4, 6 and 9 hours after intravenous and oral dosing in tubes containing EDTA and plasma was prepared by centrifugation. Samples were stored at −20° C. until analysis.

Plasma samples were pooled across collection intervals and treated with two volumes of acetonitrile. After centrifugation, the supernatent was removed and evaporated to dryness. The residues were then redissolved in 300 μl of methanol:water (1:1). Bile and urine samples from the BDC rat study were pooled across collection intervals. Bile samples were purified by sep-pak purification on C8 cartridges. The samples were evaporated and the residue was redissolved in 300 μl of methanol:water (1:1). Urine samples were diluted one to one with methanol and analyzed without further purification. All samples were analyzed by LC/UV/MS$^n$.

The HPLC system consisted of Waters alliance 2690 separation module. The column used was a Phenomenex Curosil PFP, 4.6 mm×150 mm, 5 μ particles with a flow rate of 1.0 mL/min. The mobile phase consisted of 95/5 v/v Water/Methanol containing 0.1% formic acid (Solvent A) and Methanol (Solvent B). The initial mobile phase composition was 20% Solvent B. After sample injection, this composition was held for 0.5 minute at initial conditions then ramped to 80% solvent B up to 24.5 min, and ramped to 100% solvent B up to 28 minutes. The mobile phase was then returned to initial conditions and the column re-equilibrated for 5 minutes. Total analysis time was 33 minutes.

The HPLC was interfaced to a Finnigan's Photo Diode Array Detector (PDA: UV6000) in tandem with Finnigan Deca XP ion trap mass spectrometer. Deca XP mass spectrometer was equipped with an Electrospray ionization source (ESI) interface. The source was operated in a positive ion mode with capillary temperature of 350° C. and source voltage 5.0 kV. The UV profile was extracted at λmax of 254 nm. UHP (Ultra High Purity) nitrogen was used as sheath and auxiliary gas. The normalized collision energy was set at 50% and the isolation width was 3.0 amu. Multiple MS experiments were performed in a single chromatographic run with the following data dependent settings:

Scan event 1: Full scan MS (m/z 100-m/z 1000)
Scan event 2: Data dependent scan; full scan MS/MS of most intense ion from scan 1.
Scan event 3: Data dependent scan; full scan MS$^3$ of most intense ion from scan 2.
Scan event 4: Data dependent scan; full scan MS$^4$ of most intense ion from scan 3.

The characteristic fragment ions observed in the MS$^n$ spectra of the compound of formula (I) and its metabolites are listed in Table 6 and the proposed metabolite structures are described in Table 7 and Scheme 1. The MS fragments for the compound of formula (I) listed in Table 6 were used to designate probable sites of modification in the resulting metabolites.

The mouse, rat, dog, monkey and human liver microsomes, revealed five metabolites (M2-M5 & M9) and the parent drug (P). Metabolites M2 and M5 were identified as monoxygenation product (+16 amu) of the compound of formula (I) with modifications occurring in part A and part D portions, respectively (Scheme 1). Metabolite M3 was identified as the bis-oxygenated product (+32 amu), and metabolite M4 was identified as the N-dealkylated product. The structure of metabolite M4 was confirmed by co-elution and tandem mass spectrum of the synthetic standard, compound (II). Metabolite M9 was identified as the dehydrogenated product (−2 amu) of the compound of formula (I) with introduction of a double bond on the piperazine ring. The mouse, rat, dog, monkey and human hepatocytes, showed the presence of seven metabolites (M1-M7). Metabolite M1 was identified as the monoxygenation with modification in part A of the parent molecule. Metabolites M2 to M5 were the same metabolites identified in the microsomes as discussed above. Metabolite M6, identified as the carboxylic acid metabolite of the compound of formula (I), co-eluted with the synthetic standard, compound (IV), and showed the same tandem mass spectrum as the standard. Metabolite M7 was identified as the monoxygenation product of metabolite M6. In rat plasma, the compound of formula (I) was the major peak. In plasma from rats dosed orally with the compound of formula (I), trace amounts of metabolites M4-M6, M8 and M13 were detected, whereas in plasma from rats dosed IV with the compound of formula (I), the only metabolite detected was M8. Metabolites M8 and M13 were identified as glucuronide and sulfate conjugates of the compound of formula (I) respectively. In gastrointestinal samples from rats dosed orally with the compound of formula (I), the parent was the major drug related peak with trace amounts of metabolites M2, M4 and M6.

In rat bile samples, along with the compound of formula (I) eleven metabolites, M1, M4-M8, M14, M15 and M17-M19 were detected. The identity of the various metabolites based on their fragmentation pattern is summarized in Table 6 and the proposed structures of these metabolites are described in Table 7 and in Scheme 1. The major metabolites identified in rat bile were M5 and M6.

In rat urine samples along with the compound of formula (I), seven metabolites, M1, M4-M6, M8, M11 and M12 were detected. The compound of formula (I) was present in trace amounts. The major metabolite detected in rat urine was metabolite M5.

TABLE 6

LC/MS$^n$ Analysis of the Metabolites of the compound of formula (I) in In Vitro Liver Microsomal and Hepatocyte Samples and In Vivo Plasma, Bile, Urine and GIT Samples

| Metb # | RT (min) | m/z (M + H)$^+$ | MS2 | MS3 | MS4 | Species and Matrix |
|---|---|---|---|---|---|---|
| Parent (Compound I) | 16.22 | 488 | 427, 401 | 401 to 260, 232 | 232 to 205, 161 | |
| M1 | 13.32 | 504 | 486, 417, 347 | 486 to 399, 347, 263 | 399 to 358, 260, 232, 233 | RUR, RBL, MHP |
| M2 | 13.62 | 504 | 486, 417, 347 | 486 to 399, 347, 263<br>417 to 381, 260, 232 | 399 to 358, 260, 232, 233<br>381 to 353, 260, 232, 193 | RGIT(PO), HLM, CyLM, RLM, MLM, MHP, DHP, RHP |
| M3 | 15.82 | 520 | 502, 476, 417 | 502 to 484, 458, 425, 399, 400 | 399 to 383, 359, 260, 232 | HLM, CyLM, RLM, MLM, DHP |
| M4 (Compound II) | 16.53 | 444 | 427, 401, 375, 303 | 303 to 275 | 275 to 248, 232, 204, 188, 136 | HLM, CyLM, RLM, MLM, HHP, CyHP, DHP, RUR, RBL, RPL(PO) |
| M5 | 18.18 | 504 | 460, 401, 402, 387, 375 | 460 to 442, 399, 401, 375, 319 | 442 to 399, 301, 273 | CyLM, DLM, RLM, MLM, HHP, CyHP, DHP, RHP, RPL(PO), RUR, RBL |
| M6 (Compound IV) | 18.63 | 502 | 401, 361, 333 | 401 to 260, 232 | 232 to 205, 191, 161 | HHP, CyHP, DHP, RHP, MHP, RGIT(PO), RPL(PO), RUR, RBL |
| M7 | 21.40 | 518 | 456 | 456 to 439, 427, 413, 401, 375 | 439 to 398, 298, 270, 214, 173 | HHP, CyHP, DHP, RGIT(PO), RPL(PO), RUR, RBL |
| M8 | 16.22 | 664 | 488 | 488 to 427, 401 | 401 to 260, 232 | RPL, RUR, RBL |
| M9 | 18.91 | 486 | 399, 347, 280, 263, 176 | 399 to 358, 260, 233, 232, 176 | | HLM, CyLM, RLM, MLM |
| M11 | 17.71 | 680 | 504, 460 | 504 to 460, 427, 401, 402, 375 | 402 to 385, 361, 344, 260, 232 | RUR |
| M12 | 19.93 | 504 | 417 | 417 to 381, 260, 232 | 381 to 260, 232 | RUR |

TABLE 6-continued

LC/MSⁿ Analysis of the Metabolites of the compound of formula (I) in In Vitro Liver Microsomal and Hepatocyte Samples and In Vivo Plasma, Bile, Urine and GIT Samples

| Metb # | RT (min) | m/z (M + H)+ | MS2 | MS3 | MS4 | Species and Matrix |
|---|---|---|---|---|---|---|
| M13 | 18.26 | 568 | 550, 488, 470, 427, 347 | 470 to 427, 401 | 427 to 364, 286, 258 | RPL(PO) |
| M14 | 14.07 | 462 | 444, 401, 303 | 401 to 260, 232 | 232 to 161 | RBL |
| M15 | 15.08 | 520 | 401, 79 | 401 to 260, 232 | 260 to 232 | RBL |
| M17 | 15.78 | 520 | 502, 476, 403, 363, 319 | 476 to 458 | | RBL |
| M18 | 19.13 | 504 | 460, 401 | 460 to 442, 399, 401, 375, 319 | 442 to 399, 301, 273 | RBL |
| M19 | 14.68 | 504 | 486, 417, 347 | 486 to 399, 347, 263 | 399 to 358, 260, 233 | RBL |

HLM: human liver microsomes;
RLM: rat liver microsomes;
DLM: dog liver microsomes;
MLM: mouse liver microsomes;
CyLM: cyno monkey liver microsomes;
HHP: human hepatocytes;
RHP: rat hepatocytes;
DHP: dog hepatocytes;
MHP: mouse hepatocytes;
CyHP: cyno monkey hepatocytes;
HHP: human hepatocytes,
RPL: rat plasma;
RUR: rat urine;
RBL: rat bile;
RGIT: rat gastrointestinal tract;
(M + H)+ = pseudo molecular ion in the positive ion mode of mass spectrometry.
MSⁿ = as general term to address daughter molecular ions

TABLE 7

Possible Identity of Metabolites of the compound of formula (I) were identified

| Metb # | Possible Identity | Species and Matrix |
|---|---|---|
| Parent (compound I) | | |
| M1 | mono-oxy | RUR, RBL, MHP |
| M2 | mono-oxy | RGIT(PO), HLM, CyLM, RLM, MLM, MHP, DHP, RHP, MHP |
| M3 | bis-oxy | HLM, CyLM, RLM, MLM, DHP |
| M4 (Compound II) | N-dealkylated | HLM, CyLM, RLM, MLM, HHP, CyHP, DHP, RUR, RBL, RPL(PO) |
| M5 | mono-oxy | CyLM, DLM, RLM, MLM, HHP, CyHP, DHP, RHP, RPL(PO), RUR, RBL |
| M6 (Compound IV) | carboxylic acid | HHP, CyHP, DHP, RHP, MHP, RGIT(PO), RPL(PO), RUR, RBL |
| M7 | mono-oxy M6 | HHP, CyHP, DHP, RGIT(PO), RPL(PO), RUR, RBL |
| M8 | glucuronide | RPL, RUR, RBL |
| M9 | dehydrogen-ation | HLM, CyLM, RLM, MLM |
| M11 | mono-oxy + mono-glucuronide | RUR |
| M12 | mono-oxy | RUR |
| M13 | sulfate conjugate | RPL(PO) |
| M14 | piperazine ring open | RBL |
| M15 | bis-oxy | RBL |
| M17 | bis-oxy | RBL |
| M18 | mono-oxy | RBL |
| M19 | mono-oxy | RBL |

The proposed structures of the metabolites of compound (I) are shown in Scheme 1 below.

SCHEME 1

Proposed Structures of Metabolites of compound (I)

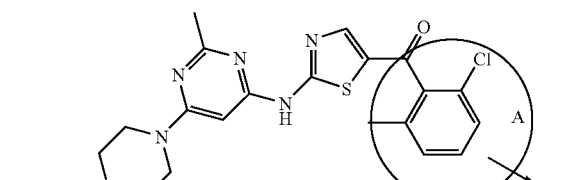

M1, M2, M12 and M19 (m/z504)
monooxidation in part A

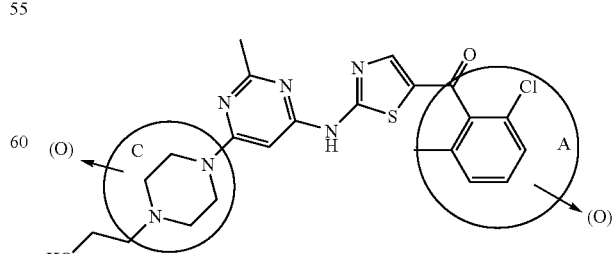

M3 (m/z520)
bis-oxidation in part A and C

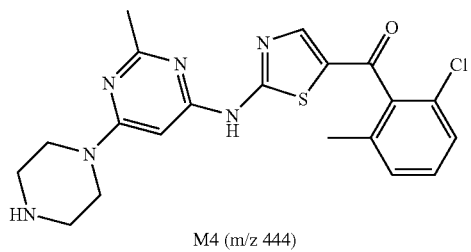
M4 (m/z 444)
N-dealkylation
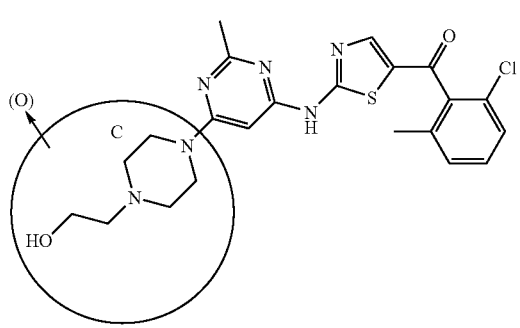
M5 and M18 (m/z 504)
mono-oxidation in part D
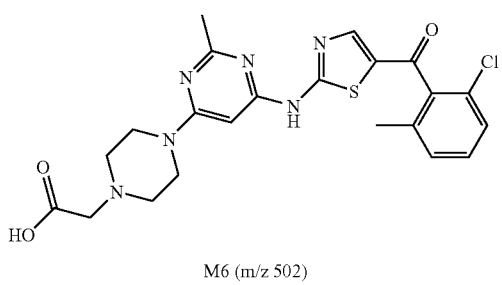
M6 (m/z 502)
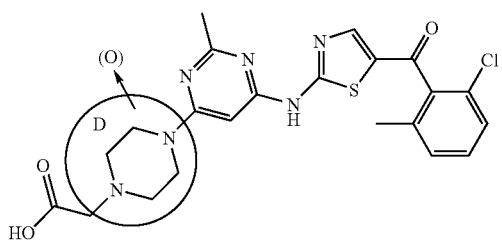
M7 (m/z 518)
mono-oxy-M6
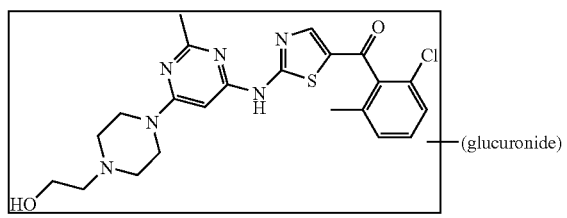
M8 (m/z 664)
glucuronide-conjugate
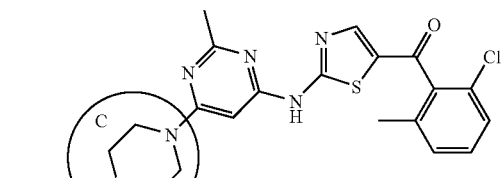
M9 (m/z 486)
dehydrogenation in part C
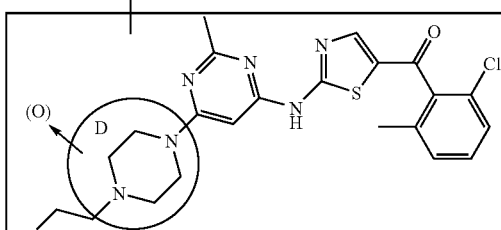
M11 (m/z 680
mon-oxy in part c and mono-glucuronide
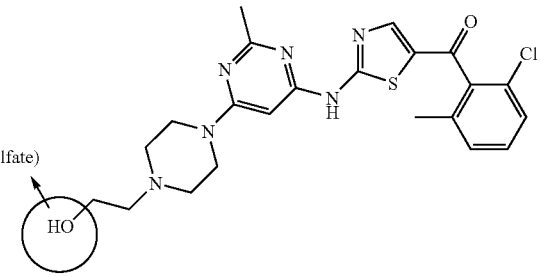
M13 (m/z 568)
sulfate conjugate
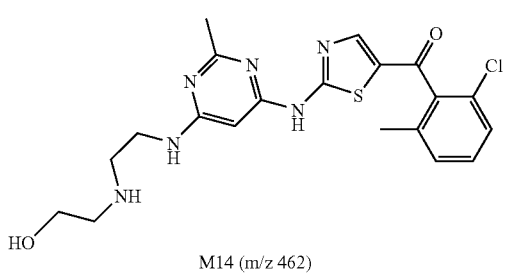
M14 (m/z 462)
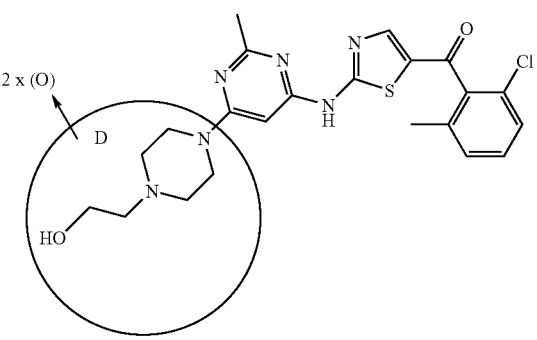
M15 (m/z 520)
bisoxidation in part D

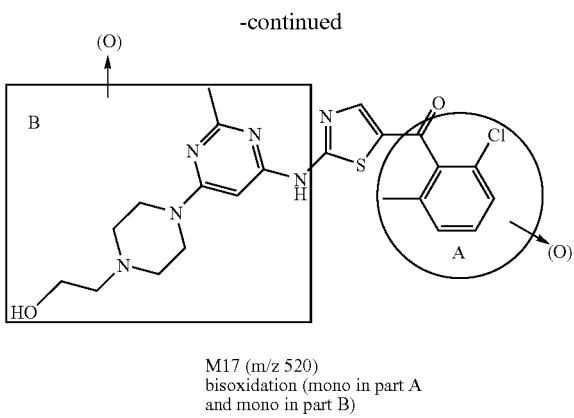

M17 (m/z 520)
bisoxidation (mono in part A and mono in part B)

Additionally, metabolites of the compound of formula (I) have been identified using the methods described below. These metabolites have been analyzed and detected using a method of analysis that was different than the two methods described above.

The compound of formula (I) was used as the [$^{14}$C] compound (Ia) (30.4 µCi/mg, radiochemical purity 99.2%), as the monohydrate of the free base. The C-14 label was on the carbon in the 2-position of the thiazole ring.

Ecolite™ liquid scintillation cocktail was purchased from ICN Biomedicals, Inc., Costa Mesa, Calif. In-Flow 2:1 liquid scintillator was from INUS Systems, Tampa, Fla. Krebs-Henseleit buffer powder (modified), potassium phosphate buffer powder, NADPH, calcium chloride dihydrate, magnesium chloride, 0.4% trypan blue solution, and D-(+)-glucose were purchased from Sigma Chemical Co., St. Louis, Mo. Gases including 95% $O_2$:5% $CO_2$ were purchased from Airgas Inc., Piscataway, N.J. Type I reagent grade water was prepared with a MilliQplus ultrapure water system (Millipore Corp, Bedford, Mass.). All chemicals used were reagent grade or better.

Freshly isolated rat hepatocyte preparations were prepared from one male Sprague-Dawley rat. Rat Hepatocytes were prepared according to a standard procedure (Seglen, PO. Preparation of isolated rat liver cells. Methods Cell Biol., 1976, 13: 29-83). Cryopreserved cynomolgus monkey hepatocytes (male, pooled, n=6) and human hepatocytes (3 individual preparation) were purchased from In Vitro Technologies (Baltimore, Md.). Microsomes from male SD Rats (pooled, n=200, 20 mg/mL) and male cynomolgus monkeys (pooled, n=8, 20 mg/mL) were obtained from Xenotech LLC, Kansas City, Kans. Human liver microsomes (male, pooled, n=38) were from BD-Gentest, Woburn, Mass.

Modified Krebs-Henseleit buffer was prepared as follows: Krebs-Henseleit buffer powder (9.6 g), sodium bicarbonate (2.1 g), glucose (1.6 g) and calcium chloride dihydrate (0.37 g) were dissolved in 700 mL of ultrapure water in a 1 L volumetric flask. Water was added to bring the volume to 1 L. The buffer was transferred to a 1 L bottle and bubbled on ice for approximately 1 h with 95% $O_2$:5% $CO_2$ (pH=7.4). Potassium phosphate buffer (1 M, pH 7.4, 25° C.) was prepared by dissolving the pre-weighed phosphate buffer powder into 380 mL of Milli-Q water.

A 6 mM stock solution of the compound of formula (Ia) (the [$^{14}$C] of the compound of formula (I) was prepared at by dissolving 3.7 mg of the compound of formula (Ia) into 1:1 acetonitrile/DMSO. The 2 mM stock solution of the compound of formula (Ia) was obtained by diluting an aliquot of the 6 mM stock solution 3-fold with acetonitrile.

Rat hepatocyte suspensions were provided at concentrations of 9.1 million cells/mL with a viability of 90%. The cell suspension was diluted accordingly with modified Krebs-Henseleit buffer to give a final concentration of 2 million cells/mL.

Human (3 vials from 3 individuals) and monkey cryopreserved hepatocytes were thawed according to the procedure provided by In Vitro Technologies. Briefly, the caps of the cryovials were loosened to release any trapped liquid nitrogen and kept on ice for 2 min. The caps were tightened and the vials were immersed in a 37° C. water bath for 75-90 sec with gentle shaking. The thawed samples (3 cryovials/~15 million cells for each 50 mL tube) were transferred into 25 mL prewarmed Krebs-Henseleit buffer in a 50 mL tube and gently inverted. The suspensions were evenly divided into 2 tubes and diluted to 40 mL with pre-warmed Krebs-Henseleit buffer. The tubes were centrifuged in an Eppendorf 5810R centrifuge (Hamburg, Germany) at 200 rpm at 4° C. for 10 min. The supernatant was discarded and the pellet gently suspended in 2 mL of Krebs-Henseleit buffer. All the tubes were combined into one tube, rinsing the empty tubes with 1 mL Krebs-Henseleit buffer. The cells were counted, checked for viability and diluted accordingly with modified Krebs-Henseleit buffer to give a final concentration of 2 million viable cells/mL.

Viability of the hepatocytes was checked using a Trypan Blue exclusion assay and a hemocytometer. A mixture of 0.1 mL of the hepatocyte suspension and 0.1 mL of trypan blue solution were diluted with 0.8 mL of Krebs-Henseleit buffer. The solution was gently mixed and plated onto a Levy hemocytometer (Hausser Scientific) and the viable cells (unstained) were counted under a light microscope. The viability of the hepatocytes ranged from 77% to 90% at the beginning of the incubations.

Hepatocyte incubations were conducted at 37° C. for 3 h in a NAPCO $CO_2$ 6000 incubator (VWR Scientific Products) under a 5% $CO_2$ atmosphere using an orbital shaker at 90 rpm. For each incubation, the final concentration of compound (Ia) was 20 µM and the hepatocyte concentrations were ~2 million cells/mL. A control incubation, in the absence of hepatocytes, was also performed for 3 h. The incubations were stopped by adding one volume of ice-cold acetonitrile. Each 0.5 mL incubation contained 0.1 M potassium phosphate buffer (pH 7.4), 2.5 mM $MgCl_2$, 2 mg/mL microsomal protein, and 2.0 mM NADPH. The final substrate concentration was 20 µM. The mixtures were incubated in a shaking water bath at 37° C. for 15 min. Control incubations in the absence of microsomes or NADPH were performed for each species. The reactions were stopped with the addition of 1 mL of ice-cold acetonitrile.

HPLC was performed on a Waters Alliance™ system equipped with Waters 2695 pumps and a photodiode array detector (Waters 2996). A Phenomenex Synergy Polar-RP® column (4.6×250 mm, 5 micron) was used for metabolite separation. All HPLC analyses were performed at 1 mL/min flow rate at room temperature. Two HPLC mobile phase and gradient systems were used because all metabolites could not be completely separated on either of the individual HPLC systems. The first system consisted of (A) water with 0.1% formic acid and (B) acetonitrile with 0.1% formic acid as mobile phase. The linear gradient was as follows: 0 min, 20% B; 1 min, 20% B; 41 min, 35% B; 42 min, 90% B; 44 min, 90% B. The column was re-equilibrated at 20% B for 6 min before the next injection. The second HPLC system was used to separate certain co-eluting metabolites that could not be separated by the first system. The mobile phase consisted of (A) water with 0.1% triflouroacetic acid (TFA) and (B) acetonitrile with 0.1% TFA. The gradient was as follows: 0 min, 20% B; 1 min, 20% B; 51 min, 35% B; 52 min, 90% B; 54 min 90% B. The column was equilibrated at 20% B for 6 min prior to the next injection.

Mass spectral analysis was performed on a Finnigan LCQ-Deca mass spectrometer equipped with an ESI probe. The LCQ-Deca was operated in the positive ion mode. High purity nitrogen was used as the sheath and the auxiliary gas with levels at 60 and 10, respectively. The capillary temperature was 275° C. Other parameters were adjusted as needed to achieve maximum sensitivity.

On-line radioactivity detection (RAD) was conducted using an INUS β-RAM detector (Model 3, INUS, Tampa, Fla.). The β-RAM was operated with a 500 μL liquid flow cell in the homogeneous liquid scintillation counting mode. A flow rate of 2 mL/min of scintillation cocktail was mixed with the HPLC effluent. The effluent from HPLC was split to the β-RAM detector (90%) and the mass spectrometer (10%) by adjusting the length and diameter of post column tubings. The β-RAM detector provided integrated output detailing the percentage and amount of radioactivity under each radioactive peak.

Hepatocyte and liver microsomal incubations were quenched with acetonitrile and were vortex-mixed for 3 min. The mixtures were centrifuged at 3500 rpm for 10 min and the supernatant were transferred into new test tubes and were dried under nitrogen in a Turbo-Vap evaporator (Zymark, Hopkinton, Mass.). Residues were reconstituted into 250 μL of 30% acetonitrile in water and aliquots of the samples were analyzed by HPLC-MS-RAD.

TABLE 8

Relative percent distribution of radioactivity in the radiochromatographic profiles of metabolites of (Ia) ([$^{14}$C] of compound (I) (20 μM) in hepatocyte and liver microsome incubations

| | % of Radioactivity in Hepatocytes | | | % of Radioactivity in Microsomes | | |
|---|---|---|---|---|---|---|
| Metabolite | Rat | Monkey | Human | Rat | Monkey | Human |
| M3a, 3b[a] | nd[b] | nd | nd | 1.4 | 6.0 | 2.9 |
| M4 (II) | 1.6 | 3.7 | 1.0 | 1.8 | 5.8 | 4.0 |
| M5 (III) | 2.7 | 3.2 | 2.3 | 37.3 | 8.6 | 4.0 |
| M6 (IV) | 4.9 | 6.5 | 9.2 | 0.7 | 2.1 | 1.6 |
| M7 | nd | 2.1 | 1.6 | nd | 0.8 | nd |
| M9a | nd | 1.4 | nd | nd | 3.2 | 1.1 |
| M20[a] (V) | 1.1 | 4.5 | 2.6 | 4.5 | 30.0 | 39.2 |
| M24[a] (VI) | | | | | | |
| M21 | 0.8 | 6.9 | 2.2 | nd | nd | nd |
| M23a, 23b[a] | nd | 1.1 | 0.6 | nd | 1.2 | nd |
| M28a, 28b[a] | nd | nd | nd | nd | 2.8 | 1.7 |
| M29a, 29b[a] | nd | nd | nd | nd | 4.9 | 4.8 |
| M29c | nd | nd | nd | nd | 2.5 | 3.8 |
| M30 | nd | 4.9 | 1.5 | nd | nd | nd |
| M31 | nd | 0.8 | nd | nd | nd | nd |
| P, (compound (I)) | 88.8 | 61.2 | 77.7 | 54.2 | 27.7 | 35.5 |
| Total | 99.9 | 96.3 | 98.7 | 99.9 | 95.6 | 98.6 |

[a]Chromatographic peaks were not well-resolved.
[b]nd = Not detected by radioactivity detection.

The structures of metabolites of compound (I) were proposed based on HPLC-MS$^n$ analysis and for M4, M5, M6, M20 and M24, comparison of retention times and MS fragmentation patterns with those of synthetic reference compounds II, III, IV, V, and VI, respectively.

Metabolites M3a and M3b both had a protonated molecular ion at m/z 520 under positive full MS scans. MS$^2$ spectra from both metabolites were nearly identical, except that M3b showed a greater propensity for loss of water upon activation in the mass spectrometer. Fragment ions at m/z 476, 417 and 363 suggested that oxidation occurred on both the piperazine and the chloromethylphenyl moieties. A loss of 33 mass units (hydroxylamine) from m/z 476 indicated the presence of an N-oxide. Based on these data, M3a and 3b were identified as positional isomers of chloromethylphenyl ring-hydroxylated derivatives of the N-oxide of compound (I).

The metabolite M7 had a molecular ion of m/z 518. MS$^2$ of m/z 518 showed one major fragment ion at m/z 456, which could be formed through the loss of water and carbon dioxide. Further fragmentation of m/z 456 (MS$^3$) showed ions at m/z 401 and 375, indicating modifications were only on the hydroxyethyl piperazine moiety. M7 was tentatively identified as a piperazine oxidized derivative of the carboxylic acid metabolite of compound (D).

The metabolite M9a showed a molecular ion at m/z 486, two mass units lower than that of the parent. Fragment ions at m/z 347, 319, and 263 in the MS$^2$ spectrum suggested the loss of 2 protons occurred on the chloromethylphenyl carboxamide moiety. The base fragment ion at m/z 399 is also consistent with the assignment. M9 was tentatively identified as a dehydrogenated derivative of compound (I).

Metabolites M23a and 23b had the same molecular ions at m/z 518. MS$^2$ spectra from both metabolites contained ions at m/z 417 and 361, suggesting hydroxylation on the chloromethylphenyl ring and formation of the carboxylic acid. A significant loss of water was only observed for M23b. M23a and M23b were not detected under the second HPLC system, possibly due to suppression of ionization by TFA. Based on the above information, M23a and 23b were tentatively identified as the positional isomers of chloromethylphenyl ring-hydroxylated derivatives of the carboxylic acid metabolite.

Metabolites M28a and 28b had the same molecular ion at m/z 460, 16 mass units higher than that of the N-dealkylated compound (I) (M4, compound II). Fragment ion at m/z 303 and 275 in the MS$^2$ spectra from both metabolites was consistent with the N-dealkylation products, and fragment ion at m/z 417 indicated hydroxylation on the chloromethylphenyl group. The degree of water loss and the intensity of fragment ion m/z 417 were the only differences observed in their MS$^2$ spectra. M28a and M28b were separated into two chromatographic peaks with the second HPLC system. M28a and M28b were tentatively identified as the positional isomers of chloromethylphenyl ring-hydroxylated M4.

Metabolites M29a, 29b, and 29c all showed a molecular ion at m/z 520 and were separated into three peaks under the first HPLC system. MS$^2$ spectra from the three metabolites all contained fragment ions at m/z 433 and 347, indicating two hydroxyl groups were added on the chloromethylphenyl moiety. MS$^3$ spectra obtained from further cleavage of m/z 433 were similar for all three metabolites, except a more significant water loss was observed for M29b. Based on these data, the three metabolites were tentatively identified as the positional isomers of dihydroxylated compound (I), with both hydroxylations occurring on the chloromethylphenyl ring.

Metabolite M30 had a molecular ion at m/z 598. The ion at m/z 518 (loss of 80 Da, a sulfate group) was also observed in full MS scans, most likely due to the in-source fragmentation of the molecular ion. Fragmentations of m/z 518 included ions at m/z 417 and 361, indicating hydroxylation on the chloromethylphenyl ring and formation of the carboxylic acid. M30 was tentatively identified as the sulfate of the chloromethylphenyl ring-hydroxylated M6.

Metabolite M31 showed a molecular ion at m/z 600. Upon activation of m/z 600, the major fragment ion at m/z 520 was formed, indicating a loss of a sulfate group. MS$^3$ spectrum of m/z 520 contained ions at m/z 433 and 347, indicating a dihydroxylation on the chloromethylphenyl ring. Therefore, M31 was tentatively identified as the sulfate of a dihydroxylated compound (I).

TABLE 9

HPLC retention time and MS fragmentations for the in vitro metabolites of compound (I)

| Metabolite | HPLC RT (min) | MH+ | Major Fragment Ions | Additional Analysis |
|---|---|---|---|---|
| P Compound (I) | 27.3 | 488 | 401, 347, 260, 232 | Synthetic standard |
| M3a, M3b | 17.6 | 520 | 502, 476, 433, 417, 363 | None |
| M4 (II) | 26.6 | 444 | 401, 303, 275 | Synthetic standard |
| M5 (III) | 31.0 | 504 | 460, 401, 363 | Synthetic standard |
| M6 (IV) | 25.2 | 502 | 458, 401, 361, 333 | Synthetic standard |

TABLE 9-continued

HPLC retention time and MS fragmentations for the in vitro metabolites of compound (I)

| Metabolite | HPLC RT (min) | MH+ | Major Fragment Ions | Additional Analysis |
|---|---|---|---|---|
| M7 | 35.3 | 518 | 456, 439, 401, 315 | None |
| M9a | 45.1 | 486 | 399, 347, 319, 263 | None |
| M20 (V) | 14.7 | 504 | 417, 347, 319 | NMR |
| M21 | 8.5 | 584 | 504, 417, 347 | None |
| M23a, M23b | 13.3 | 518 | 500, 417, 361, 333 | None |
| M24 (VI) | 14.7 | 504 | 486, 417, 399, 347 | NMR |
| M28a, M28b | 13.7 | 460 | 442, 417, 303, 275 | None |
| M29a, M29b, M29c | 8.3-10.2 | 520 | 502, 433, 397, 347 | None |
| M30 | 6.9 | 598 | 518, 417, 361, 333 | None |
| M31 | 10.7 | 600 | 520, 433, 397, 347 | None |

TABLE 10

Proposed Structures of Metabolites[a]

| Metabolite | Structure |
|---|---|
| M3a, M3b | 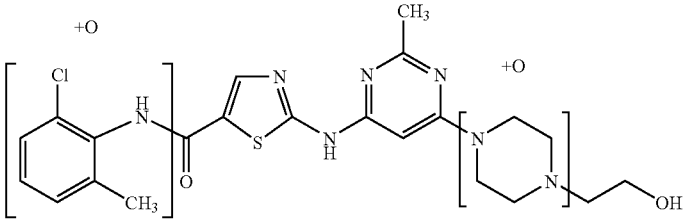 |
| M9a | 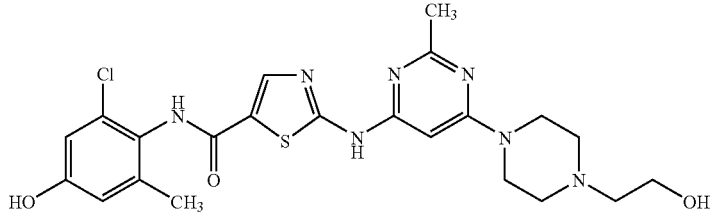 |
| M20[b] | 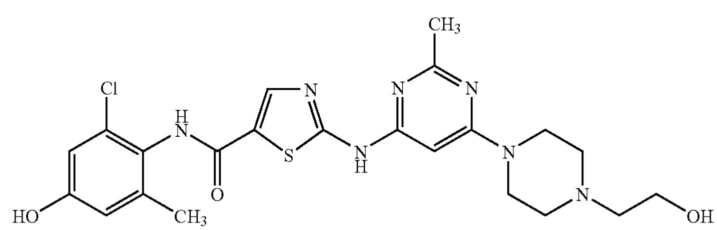 |
| M23a, M23b | 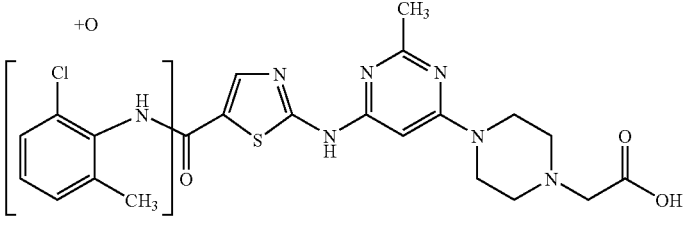 |

TABLE 10-continued

Proposed Structures of Metabolites[a]

| Metabolite | Structure |
|---|---|
| M24[b] | (structure: 2-chloro-6-(hydroxymethyl)phenyl thiazole carboxamide linked to 2-methylpyrimidine with 4-(2-hydroxyethyl)piperazine) |
| M28a, M28b | +O (structure: chloro-methylphenyl thiazole carboxamide linked to 2-methylpyrimidine with piperazine-NH) |
| M29a, M29b, M29c | +2O (structure: chloro-methylphenyl thiazole carboxamide linked to 2-methylpyrimidine with 4-(2-hydroxyethyl)piperazine) |
| M30 | +O, +SO₃ (structure: chloro-methylphenyl thiazole carboxamide linked to 2-methylpyrimidine with piperazine-CH₂COOH) |
| M31 | +2O ... +SO₃ (structure: chloro-methylphenyl thiazole carboxamide linked to 2-methylpyrimidine with 4-(2-hydroxyethyl)piperazine) |

[a]Structures previously presented were omitted from this table.
[b]The exact structures of metabolites M20 and M24 were determined in this study based on their analytical comparison to compounds (V) and (VI), respectively.

Additionally, metabolites of the compound of formula (I) have been identified using the methods described below. These metabolites have been analyzed and detected using different method of analysis as were described above.

Urine, feces, and plasma samples were obtained from three studies following single oral doses of [$^{14}$C] compound (I) (compound (Ia)) to rats, monkeys, and humans.

In the rat study, two groups of male Sprague-Dawley rats were dosed orally with compound Ia (the [$^{14}$C] of compound (I) (15 mg/kg, 6.7 μCi/mg) dissolved in 80 mM citrate buffer (pH 3.1). Plasma samples (1, 4, 8, and 24 h) were obtained from rats in group 1 (three rats per collection time). Urine (collected at 0-6, 6-12, 12-24, and at 24 h intervals up to 168 h) and feces (collected from 0-168 h at 24 h intervals) were obtained from rats in group 2 (n=3).

In the monkey study, plasma (1, 4, 8, 24 and 96 h), urine (0-6, 6-12, 12-24, and at 24 h intervals up to 168 h) and feces (0-168 h at 24 h intervals) were obtained from three male cynomolgus monkeys following single 10 mg/kg (3.0 µCi/mg) oral dose. A separate bile-duct cannulated (BDC) monkey study was also conducted. Bile (0-4,4-8, 8-24, 24-48, and 48-72 h) and urine (0-8,8-24, 24-48, and 48-72 h) were collected following single IV infusion of [$^{14}$C] compound (I) (2 mg/kg, 15.0 µCi/mg) in 80 mM citrate buffer to three BDC monkeys.

In the human study, plasma (1, 2, 4, 8, 12 and 24 h), urine (0-12, 12-24, and at 24 h intervals up to 312 h) and feces (0-312 h at 24 h intervals) were obtained from eight healthy male subjects following single 100-mg oral doses (120 µCi) of the [$^{14}$C] of compound (I).

Representative pooled urine and fecal homogenate samples for biotransformation profiling from rats (5% pool, 0-168 h), monkeys (5% pool, 0-168 h), BDC monkeys (5% pool, 0-72 h for both urine and bile) and humans (1% pool, 0-168 h) were prepared by combining a constant percentage of volume or weight excreted during each collection interval. Plasma samples were segregated by collection time and equal volumes of individual plasma samples at a given time point were combined for biotransformation profiling.

The [$^{14}$C] of compound (I) (compound Ia) (17.0 µCi/mg, radiochemical purity 99.5%) was used as the monohydrate of the free base. The C-14 label was on the carbon-2 of the thiazole ring.

Ecolite™ liquid scintillation cocktail was purchased from ICN Biomedicals, Inc., Costa Mesa, Calif. Type I reagent grade water was prepared with a MilliQplus ultrapure water system (Millipore Corp, Bedford, Mass.). All chemicals used were reagent grade or better.

HPLC was performed on an Agilent 1100™ system equipped with binary pumps, autoinjector, and a column heater. A Phenomenex Synergy Polar-RP® column (4.6×250 mm, 5 micron) was used for metabolite separation. All HPLC analyses were performed at 1 mL/min flow rate at 35° C. The HPLC mobile phase consisted of (A) water with 0.1% formic acid and (B) acetonitrile with 0.1% formic acid. The linear gradient was as follows: 0 min, 15% B; 3 min, 15% B; 53 min, 32% B; 53.5 min, 32% B; 60 min, 90% B; 63, 90% B. The column was re-equilibrated at 15% B for 6 min before the next injection.

For quantification of radioactivity, HPLC effluent was collected in 15-sec intervals on 96-well Packard Lumaplates® with a Gilson Model FC 204 fraction collector (Gilson, Middleton, Wis.). Each fraction of column eluent was evaporated to dryness on a Savant Speed-Vac (Savant Instruments Inc., Holbrook, N.Y.) and counted for radioactivity with a Packard Top Count® microplate scintillation analyzer (Packard Biosciences, Downers Grove, Ill.).

The volumes of pooled plasma processed for HPLC analysis for rat, monkey and human ranged between 1.5 and 8.0 mL. Pooled plasma samples were extracted with methanol/acetonitrile (1:1) at a ratio of 2 volumes solvent to 1 volume of plasma. The mixtures were vortex mixed, sonicated for 5 min, and centrifuged at 3500 rpm for 10 min. The supernatants were transferred into new tubes. The remaining pellets were extracted two more times with 3 mL of methanol/acetonitrile (1:1). The supernatants were combined and evaporated to dryness in a Savant Speed-Vac (Savant Instruments, Inc., Holbrook, N.Y.). The residue was reconstituted into 0.35 to 0.45 mL of 30% acetonitrile in water, vortex mixed and centrifuged at 13000 rpm for 5 min (American Scientific Products Biofuge A centrifuge, Heraeus Sepatech GmbH, Germany). The supernatant was injected onto the HPLC for profiling. Aliquots of the reconstituted samples (30 µl) were also counted on the liquid scintillation counter (LSC) to determine the recovery of radioactivity.

The pooled monkey and human urine samples (3-5 mL) were extracted with 2 volumes of acetonitrile/acetone (1:1). The mixtures were vortex mixed, sonicated and centrifuged at 3500 rpm for 10 min. The supernatants were evaporated to dryness. The residue was suspended in 0.3-0.5 mL of 30% acetonitrile in water and centrifuged at 13000 rpm for 5 min. Aliquots of the supernatants were injected onto the HPLC or analyzed by LSC for radioactivity recovery. Pooled urine samples from BDC monkeys and rats were centrifuged at 13000 rpm for 10 min and injected onto the HPLC for profiling without further treatment.

A pooled bile sample (0-72 h) from BDC monkeys was diluted fifteen-fold with 20% acetonitrile in water with 0.1% formic acid. The diluted sample was centrifuged at 13000 rpm for 5 min. Aliquots of the supernatant was injected onto HPLC or analyzed by LSC for radioactivity recovery.

The amount of fecal homogenate used for analysis was 0.20, 0.19 and 0.51 g for rat, monkey and human, respectively. Each pooled fecal homogenate was extracted by addition of 3 volumes of acetonitrile/methanol (1:1) to 1 volume of fecal homogenate and mixed on a vortex mixer. The mixture was sonicated for 5 min and then centrifuged at 3000 rpm for 10 min. The supernatants were removed and saved. The extraction was repeated two additional times and the supernatants were combined and evaporated to dryness on a Savant Speed-Vac. The residue was suspended in 0.5 mL of the 35% acetonitrile in water, vortex mixed for 5 min and centrifuged at 13000 rpm for 10 min. An aliquot of the supernatant was injected onto the HPLC or analyzed by LSC for radioactivity recovery.

The LC/MS system used for analysis of plasma, urine, bile, and fecal samples consisted of an Agilent 1100™ HPLC system connected to a Finnigan LCQ-DecaXP mass spectrometer. Samples were analyzed using positive electrospray ionization. The capillary temperature used for analysis was 320° C., and the nitrogen gas flow rate, spray current, and voltages were adjusted to give maximum sensitivity. The HPLC conditions were described in section 3.3.1.

Counts per min (CPM) were determined on a Packard TopCount NXT microplate scintillation and luminescence counter. For each injection, the average CPM value (2-4 CPM) obtained from fractions between 2-3 min (column void) in the chromatogram was subtracted from the CPM value of each fraction. Biotransformation profiles were prepared by plotting the background subtracted CPM values against time-after-injection. Radioactivity peaks in the biotransformation profiles were reported as a percentage of the total radioactivity (after background subtraction) collected during the entire HPLC run.

The structures of metabolites of compound (I) were proposed based on HPLC-MS$^n$ analysis and where available, retention times and MS fragmentation patterns were compared with those of the synthetic standards. A summary of HPLC retention times and prominent fragment ions of all the in vivo metabolites are presented in Table 15. The structures of metabolites are shown in Table 16.

Metabolites M8a, M8b, and M8c all had a protonated molecular ion at m/z 664 under positive full MS scans, indicating they are isomers. M8a, M8b, and M8c were detected as three separate peaks. MS$^2$ spectra from all three metabolites were identical, all showing a neutral 176 Da loss indicating they are glucuronides. Fragment ions at m/z 488 and 401 suggested that no other modifications had occurred to the parent molecule. Based on these data, M8a, M8b, and M8c were identified as positional isomers of glucuronide conjugates of compound (I).

Metabolites M23a and M23b had the same molecular ion at m/z 518. The two metabolites were detected in in vitro studies, but they were not well separated under the in vitro HPLC conditions described above. Under the current HPLC system, M23a and M23b were resolved into two distinct chromatographic peaks on MS total ion chromatogram. $MS^2$ spectra from both metabolites contained ions at m/z 417 and 361, suggesting hydroxylation on the chloromethylphenyl ring and formation of the carboxylic acid. A significant loss of water (m/z 500) was only observed for M23b indicating hydroxylation on M23b is likely to be on the methyl group. Based on the above information, M23a and 23b were tentatively identified as the positional isomers of chloromethylphenyl ring-hydroxylated derivatives of the carboxylic acid metabolite.

Metabolite M34 showed a molecular ion of m/z 534, 46 Da higher than that of the parent molecule. Major fragment ions of m/z 534 included ions at m/z 472, 403, 377, and 333. Fragment ions at m/z 377 and 333 suggested the formation of a carboxylic acid and piperazine N-oxidation. Fragment ions at m/z 472 and 403 indicated hydroxylation at chloromethylphenyl ring. M34 was tentatively identified as an oxidized metabolite of compound (I) with oxidations at three positions of the molecule: the hydroxyethyl, the piperazine ring, and the chloromethylphenyl ring.

Metabolite M35a and M35b both had a protonated molecular ion at m/z 662 under positive full MS scans, indicating they are isomers. $MS^2$ spectra from both metabolites were identical and contained a neutral 176 Da loss indicating they are glucuronide conjugates. Fragment ions at m/z 486 and 399 suggested two Da was lost from the parent molecule, and m/z 347 suggested the dehydrogenation had occurred on the chloromethylphenyl carboxamide group. Based on these data, M35a and M35b were identified as positional isomers of glucuronides of a dehydrogenated compound (I).

Metabolite M36 had a molecular ion at m/z 694. $MS^2$ spectra of m/z 694 contained a major fragment ion at m/z 518. The neutral 176 Da loss from m/z 694 indicated that M36 is a glucuronide conjugate. Further fragmentations of m/z 518 included ions at m/z 417 and 361, indicating hydroxylation on the chloromethylphenyl ring and formation of the carboxylic acid. M36 was tentatively identified as the glucuronide of the chloromethylphenyl ring-hydroxylated carboxylic acid derivative of compound (I).

Metabolite M37a and M37b both had a molecular ion at m/z 680. $MS^2$ spectra of m/z 680 for both metabolites contained a major fragment ion at m/z 504 (neutral 176 Da loss) indicating both metabolites were glucuronides. $MS^3$ spectra of m/z 504 from both metabolites contained ions at m/z 417 and 347, suggesting hydroxylation on the chloromethylphenyl ring. A significant loss of water (m/z 486) was only observed for M37b indicating hydroxylation on M37b is likely to be on the methyl group. Based on the above information, M37a and M37b were tentatively identified as positional isomers of glucuronides of chloromethylphenyl ring-hydroxylated compound (I).

TABLE 11

Relative percent distribution of radioactive metabolites in pooled plasma samples after oral administration of [$^{14}$C] compound (I) to rats, monkeys, and humans

| Metabolite | % Distribution | | |
|---|---|---|---|
| | Rat (4 h) | Monkey (4 h) | Human (2 h) |
| M3a, b[b] | nd | 1.4 | 3.3 |
| M4 (II) | 2.6 | 3.0 | MS[e] |
| M5 (III) | 18.7 | 2.6 | 4.5 |
| M6 (IV) | 2.2 | 2.7 | 3.6 |

TABLE 11-continued

Relative percent distribution of radioactive metabolites in pooled plasma samples after oral administration of [$^{14}$C] compound (I) to rats, monkeys, and humans

| Metabolite | % Distribution | | |
|---|---|---|---|
| | Rat (4 h) | Monkey (4 h) | Human (2 h) |
| M7 | nd | 2.1 | 3.3 |
| M8a | nd | 12.8 | 3.4 |
| M8b, M23a, b[b,c] | nd | 4.5[c] | 1.4[c] |
| M8c, M13[d] | 17.6[d] | nd | nd |
| M20 (V) | nd | 2.8 | 12.5 |
| M21 | nd | 4.7 | 9.5 |
| M24 (VI) | nd | 0.7 | 3.1 |
| M30 | nd | 9.7 | 6.9 |
| M31 | nd | 1.7 | 3.6 |
| M34 | nd | 1.4 | 1.1 |
| M35a | nd | MS[e] | 3.6 |
| M37a, b[b] | nd | 3.7 | 4.1 |
| Parent (I) | 52.8 | 32.1 | 25.5 |
| Total | 93.9 | 85.9 | 89.4 |

[b]Metabolites M3a, b, M23a, b and M37a, b were positional isomers and were not well resolved on HPLC.
[c]Metabolites M8b and M23a, b were not well resolved on HPLC. The % of distribution is the total percentage of all three metabolites.
[d]Metabolites M8c and M13 were not well resolved on HPLC. The % of distribution is the total percentage of the two metabolites.
[e]Metabolite M35a was only detected by mass spectrometry in monkey plasma.
nd, Not detected.

TABLE 12

Relative percent distribution of radioactive metabolites in pooled urine samples after oral administration of [$^{14}$C] of compound (I) to rats, monkeys, and humans

| | Metabolites in Urine (0-168 hr) | | | | | |
|---|---|---|---|---|---|---|
| | Rat | | Monkey | | Human | |
| Metabolite | % Rad[b] | % Dose | % Rad | % Dose | % Rad | % Dose |
| M3a, b[c] | 2.3 | 0.1 | 4.1 | 0.1 | 6.8 | 0.2 |
| M4 (II) | 4.4 | 0.3 | 1.7 | 0.05 | 1.3 | 0.05 |
| M5 (III) | 52.4 | 3.4 | 35.8 | 1.1 | 39.8 | 1.4 |
| M6 (IV) | 6.5 | 0.4 | 2.2 | 0.06 | 1.3 | 0.05 |
| M7 | 0.3 | 0.02 | 10.3 | 0.3 | 2.1 | 0.08 |
| M8a | 0.9 | 0.06 | 1.2 | 0.04 | 5.5 | 0.2 |
| M8b | 0.8 | 0.05 | 2.3 | 0.07 | nd | nd |
| M20 (V) | 9.9 | 0.6 | 0.6 | 0.02 | 4.1 | 0.2 |
| M21 | 1.5 | 0.1 | 2.7 | 0.08 | 7.8 | 0.3 |
| M24 (VI) | nd | nd | 1.9 | 0.06 | 6.0 | 0.2 |
| M34 | nd | nd | 3.9 | 0.1 | 2.3 | 0.08 |
| M35a | nd | nd | nd | nd | 4.2 | 0.2 |
| M36 | nd | nd | nd | nd | 4.4 | 0.2 |
| M37a, b[c] | nd | nd | nd | nd | 2.5 | 0.1 |
| Parent (I) | 11.6 | 0.7 | 21.2 | 0.6 | 3.6 | 0.1 |
| Total | 90.6 | 5.7 | 87.9 | 2.6 | 91.7 | 3.4 |

[b]% of total radioactivity in sample.
[c]These metabolites are positional isomers that were not well resolved on HPLC.
nd, Not detected.

TABLE 13

Relative percent distribution of radioactive metabolites in pooled fecal extracts after oral administration of [$^{14}$C] of compound (I) to rats, monkeys, and humans

| | Metabolites in Feces (0-168 hr) | | | | | |
|---|---|---|---|---|---|---|
| | Rat | | Monkey | | Human | |
| Metabolite | % Rad[b] | % Dose | % Rad | % Dose | % Rad | % Dose |
| M4 (II) | 2.5 | 1.9 | 3.8 | 2.9 | 3.1 | 2.6 |
| M6 (IV) | 17.3 | 13.2 | 18.2 | 14.0 | 10.4 | 8.9 |
| M7 | 1.0 | 0.8 | 0.5 | 0.4 | nd | nd |
| M9a | nd | nd | 1.7 | 1.3 | 1.8 | 1.5 |
| M20 (V) | 9.9 | 7.6 | 15.2 | 11.7 | 36.6 | 31.2 |
| M23a, b[c] | 3.8 | 2.9 | 12.6 | 9.7 | 14.7 | 12.5 |
| M24 (VI) | 4.0 | 3.1 | 8.6 | 6.6 | 4.7 | 4.0 |
| Parent (I) | 54.5 | 41.6 | 32.2 | 24.7 | 22.4 | 19.1 |
| Total | 93.0 | 71.1 | 92.8 | 71.3 | 93.7 | 79.8 |

[b]% of total radioactivity in sample.
[c]These metabolites positional isomers that were not well resolved on HPLC.
nd, Not detected.

TABLE 14

Relative percent distribution of radioactive metabolites in urine and bile after IV administration of [$^{14}$C] compound (I) to bile-duct cannulated monkeys

| | Metabolites in BDC-Monkeys (0-72 hr) | | | |
|---|---|---|---|---|
| | Urine | | Bile | |
| Metabolite | % Rad[b] | % Dose | % Rad | % Dose |
| M3a, b[c] | 4.3 | 0.4 | 3.0 | 2.0 |
| M4 (II) | nd | nd | 0.7 | 0.5 |
| M5 (III) | 70.7 | 7.0 | 7.4 | 5.0 |
| M6 (IV) | 2.8 | 0.3 | 9.4 | 6.3 |
| M7 | 9.5 | 0.9 | 12.4 | 8.3 |
| M8a | nd | nd | 1.4 | 0.9 |
| M8b, M23a, b[c,d] | nd | nd | 4.6[d] | 3.1[d] |
| M20 (V) | 2.7 | 0.3 | 3.5 | 2.4 |
| M21 | nd | nd | 13.3 | 8.9 |
| M24 (VI) | 1.4 | 0.1 | 4.4 | 3.0 |
| M30 | nd | nd | 9.1 | 6.1 |
| M31 | nd | nd | 4.8 | 3.2 |
| M34 | 2.6 | 0.3 | 5.1 | 3.4 |
| M35a | nd | nd | MS[e] | MS[e] |
| M35b | nd | nd | 3.2 | 2.2 |
| M36 | nd | nd | 1.3 | 0.9 |
| M37a, b[c] | nd | nd | 1.7 | 1.1 |
| Parent (I) | 1.4 | 0.1 | 4.7 | 3.2 |
| Total | 95.4 | 9.4 | 90.0 | 60.5 |

[b]% of total radioactivity in sample.
[c]These metabolites are positional isomers that were not well resolved on HPLC.
[d]Metabolites M8b and M23a, b were not well resolved on HPLC. The % of distribution is the total percentage of all three metabolites.
[e]Metabolite was only detected by mass spectrometry
nd, Not detected.

TABLE 15

HPLC retention time and MS fragmentations for the in vivo metabolites of compound (I)

| Metabolite | HPLC RT (min) | MH+ | Major Fragment Ions | Additional Analysis |
|---|---|---|---|---|
| P Compound (I) | 41.5 | 488 | 401, 347, 260, 232 | Synthetic standard |
| M3a, M3b | 29-30 | 520 | 502, 476, 433, 417, 363 | None |
| M4 (II) | 40.2 | 444 | 401, 303, 275 | Synthetic standard |
| M5 (III) | 45.3 | 504 | 460, 401, 363 | Synthetic standard |
| M6 (IV) | 39.4 | 502 | 458, 401, 361, 333 | Synthetic standard |
| M7 | 51.4 | 518 | 456, 439, 401, 315 | None |
| M8a, M8b, M8c | 11.1, 24.4, 35.5 | 664 | 488, 401, 347, 319 | None |
| M9a | 59.4 | 486 | 399, 347, 263 | None |
| M13 | 35.2 | 568 | 488, 401, 347, 319 | None |
| M20 (V) | 25.3 | 504 | 417, 347, 319 | NMR |
| M21 | 17.1 | 584 | 504, 417, 347 | None |
| M23a, M23b | 24.5-25.5 | 518 | 500, 417, 361, 333 | None |
| M24 (VI) | 26.0 | 504 | 486, 417, 399, 347 | NMR |
| M30 | 15.9 | 598 | 518, 417, 361, 333 | None |
| M31 | 21.1 | 600 | 520, 433, 397, 347 | None |
| M34 | 35.7 | 534 | 472, 403, 377, 333 | None |
| M35a, M35b | 21.2, 43.1 | 662 | 486, 399, 347, 319 | None |
| M36 | 10.2 | 694 | 518, 417, 361, 333 | None |
| M37a, M37b | 11.2, 13.1 | 680 | 504, 486, 417, 347 | None |

TABLE 16

Proposed Structures of Metabolites[a]

| Metabolite | Structure |
|---|---|
| M8a, M8b, M8c | 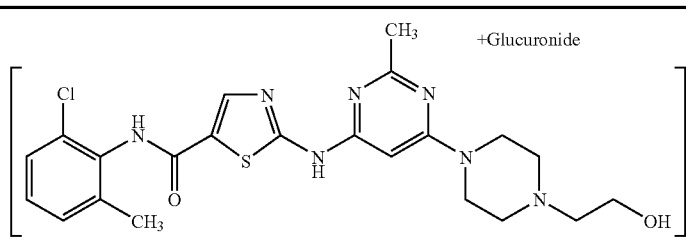 |

TABLE 16-continued

Proposed Structures of Metabolites[a]

| Metabolite | Structure |
|---|---|
| M34 | [+O, chlorophenyl-methyl-NH-C(=O)-thiazole-NH-pyrimidine(CH3)-piperazine-N(→O)-CH2-C(=O)OH] |
| M35a, M35b | +Glucuronide [−2H, chlorophenyl-methyl-NH-C(=O)-thiazole-NH-pyrimidine(CH3)-piperazine-N-CH2-C(=O)OH] M35a, b |
| M36 | +Glucuronide [+O, chlorophenyl-methyl-NH-C(=O)-thiazole-NH-pyrimidine(CH3)-piperazine-N-CH2-C(=O)OH] |
| M37a, M37b | +Glucuronide [+O, chlorophenyl-methyl-NH-C(=O)-thiazole-NH-pyrimidine(CH3)-piperazine-N-CH2CH2-OH] |

[a]Structures previously presented were not included in this table.

Utility

The metabolites of the compound of formula (I) prepared according to the inventive process herein may inhibit protein tyrosine kinases, especially Src-family kinases such as Lck, Fyn, Lyn, Src, Yes, Hck, Fgr and Blk, and are thus useful in the treatment, including prevention and therapy, of protein tyrosine kinase-associated disorders such as immunologic and oncologic disorders. The metabolites of the compound of formula (I) also may inhibit receptor tyrosine kinases including HER1 and HER2 and therefore be useful in the treatment of proliferative disorders such as psoriasis and cancer. The ability of these compounds to inhibit HER1 and other receptor kinases will permit their use as anti-angiogenic agents to treat disorders such as cancer and diabetic retinopathy. "Protein tyrosine kinase-associated disorders" are those disorders which result from aberrant tyrosine kinase activity, and/or which are alleviated by the inhibition of one or more of these enzymes. For example, Lck inhibitors are of value in the treatment of a number of such disorders (for example, the treatment of autoimmune diseases), as Lck inhibition blocks T cell activation. The treatment of T cell mediated diseases, including inhibition of T cell activation and proliferation, is a particularly preferred use for compounds of formula (I) prepared according to the process herein.

Use of the metabolites of the compound of formula (I) in treating protein tyrosine kinase-associated disorders is exemplified by, but is not limited to, treating a range of disorders such as: transplant (such as organ transplant, acute transplant or heterograft or homograft (such as is employed in burn treatment)) rejection; protection from ischemic or reperfusion injury such as ischemic or reperfusion injury incurred during organ transplantation, myocardial infarction, stroke or other causes; transplantation tolerance induction; arthritis (such as rheumatoid arthritis, psoriatic arthritis or osteoarthritis); multiple sclerosis; chronic obstructive pulmonary disease (COPD), such as emphysema; inflammatory bowel disease, including ulcerative colitis and Crohn's disease; lupus (systemic lupus erythematosis); graft vs. host disease; T-cell mediated hypersensitivity diseases, including contact hypersensitivity, delayed-type hypersensitivity, and gluten-sensitive enteropathy (Celiac disease); psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; cancers, including cancers where Lck or other Src-family kinases such as Src are activated or overexpressed, such as colon carcinoma and thymoma, and cancers where Src-family kinase activity facilitates tumor growth or survival; glomerulonephritis; serum sickness; uticaria; allergic diseases such as respiratory allergies (asthma, hayfever, allergic rhinitis) or skin allergies; scleracierma; mycosis fungoides; acute inflammatory responses (such as acute respiratory distress syndrome and ishchemia/reperfusion injury); dermatomyositis; alopecia greata; chronic actinic dermatitis; eczema; Behcet's disease; Pustulosis palmoplanteris; Pyoderma gangrenum; Sezary's syndrome; atopic dermatitis; systemic schlerosis; and morphea.

The compounds of the present invention are useful for the treatment of cancers such as chronic myelogenous leukemia (CML), gastrointestinal stromal tumor (GIST), small cell lung cancer (SCLC), non-small cell lung cancer (NSCLC), ovarian cancer, melanoma, mastocytosis, germ cell tumors, acute myelogenous leukemia (AML), pediatric sarcomas, breast cancer, colorectal cancer, pancreatic cancer, prostate cancer and others known to be associated with protein tyrosine kinases such as, for example, SRC, BCR-ABL and c-KIT. The compounds of the present invention are also useful in the treatment of cancers that are sensitive to and resistant to, and/or to patients who are intolerant to, chemotherapeutic agents that target BCR-ABL and c-KIT, such as, for example, Gleevec® (STI-571) and AMN-107.

In another embodiment of the invention compounds are administered in conjunction with at least one anti-neoplastic agent.

As used herein, the phrase "anti-neoplastic agent" or "anti-cancer agent" is synonymous with "chemotherapeutic agent" and/or "anti-proliferative agent" and refers to compounds that prevent cancer, or hyperproliferative cells from multiplying. Anti-proliferative agents prevent cancer cells from multiplying by: (1) interfering with the cell's ability to replicate DNA and (2) inducing cell death and/or apoptosis in the cancer cells.

Classes of compounds that may be used as anti-proliferative cytotoxic agents and/or anti-proliferative agents include the following:

Alkylating agents (including, without limitation, nitrogen mustards, ethylenimine derivatives, alkyl sulfonates, nitrosoureas and triazenes): Uracil mustard, Chlormethine, Cyclophosphamide (Cytoxan®), Ifosfamide, Melphalan, Chlorambucil, Pipobroman, Triethylenemelamine, Triethylenethiophosphoramine, Busulfan, Carmustine, Lomustine, Streptozocin, Dacarbazine, and Temozolomide.

Antimetabolites (including, without limitation, folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine.

Natural products and their derivatives (for example, vinca alkaloids, antitumor antibiotics, enzymes, lymphokines and epipodophyllotoxins): Vinblastine, Vincristine, Vindesine, Bleomycin, Dactinomycin, Daunorubicin, Doxorubicin, Epirubicin, Idarubicin, Ara-C, paclitaxel (paclitaxel is commercially available as Taxol®), Mithramycin, Deoxyco-formycin, Mitomycin-C, L-Asparaginase, Interferons (especially IFN-a), Etoposide, and Teniposide.

Other anti-proliferative cytotoxic agents and/or anti-proliferative agents are navelbene, CPT-11, anastrazole, letrazole, capecitabine, reloxafine, cyclophosphamide, ifosamide, and droloxafine.

The phrase "radiation therapy" includes, but is not limited to, x-rays or gamma rays which are delivered from either an externally applied source such as a beam or by implantation of small radioactive sources. Radiation therapy may be useful in combination with the compound of the present invention.

The following may also be useful when administered in combination with the compound of the present invention.

Microtubule affecting agents interfere with cellular mitosis and are well known in the art for their anti-proliferative cytotoxic activity. Microtubule affecting agents useful in the invention include, but are not limited to, allocolchicine (NSC 406042), Halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol®, NSC 125973), Taxol® derivatives (e.g., derivatives (e.g., NSC 608832), thiocolchicine NSC 361792), trityl cysteine (NSC 83265), vinblastine sulfate (NSC 49842), vincristine sulfate (NSC 67574), natural and synthetic epothilones including but not limited to epothilone A, epothilone B, epothilone C, epothilone D, desoxyepothilone A, desoxyepothilone B, [1S-[1R*,3R*(E), 7R*,10S*,11R*,12R*,16S*]]-7-1'-dihydroxy-8,8,10,12,16-pentamethyl-3-[1-methyl-2-(2-methyl-4-thiazolyl)ethenyl]-4-aza-17 oxabicyclo [14.1.0]heptadecane-5,9-dione (disclosed in U.S. Pat. No. 6,262,094, issued Jul. 17, 2001), [1S-[1R*,3R*(E),7R*,10S*,11R*,12R*,16S*]]-3-[2-[2-(aminomethyl)-4-thiazolyl]-1-methylethenyl]-7,11-dihydroxy-8,8,10,12,16-pentamethyl-4-17-dioxabicyclo [14.1.0]-heptadecane-5,9-dione (disclosed in U.S. Ser. No. 09/506,481 filed on Feb. 17, 2000, and examples 7 and 8 herein), [1S 1R*,3R*(E),7R*,10S*,11R*,12R*, 16S*]]-7, 11-dihydroxy-8,8,10,12,16-pentamethyl-3-[1-methyl-2-(2-methyl-4-thiazolyl)ethenyl]-4-aza-17oxabicyclo[14.1.0]-heptadecane-5,9-dione, [1S-[1R*,3R*(E),7R*,10S*,11R*, 12R*,16S*]]-3-[2-[2-(Aminomethyl)-4-thiazolyl]-1-methylethenyl]-7,11-dihydroxy-8,8,10,12,16-pentamethyl-4,17-dioxabicyclo[14.1.0]heptadecane-5,9-dione, and derivatives thereof; and other microtubule-disruptor agents. Additional antineoplastic agents include, discodermolide (see Service, (1996) Science, 274:2009) estramustine, nocodazole, MAP4, and the like. Examples of such agents are also described in the scientific and patent literature, see, e.g., Bulinski (1997) J. Cell Sci. 110:3055 3064; Panda (1997) Proc. Natl. Acad. Sci. USA 94:10560-10564; Muhlradt (1997) Cancer Res. 57:3344-3346; Nicolaou (1997) Nature 387:268-272; Vasquez (1997) Mol. Biol. Cell. 8:973-985; Panda (1996) J. Biol. Chem 271:29807-29812.

In cases where it is desirable to render aberrantly proliferative cells quiescent in conjunction with or prior to treatment with the chemotherapeutic methods of the invention, hormones and steroids (including synthetic analogs): 17a-Ethinylestradiol, Diethylstilbestrol, Testosterone, Prednisone, Fluoxymesterone, Dromostanolone propionate, Testolactone, Megestrolacetate, Methylprednisolone, Methyl-testosterone, Prednisolone, Triamcinolone, hlorotrianisene, Hydroxyprogesterone, Aminoglutethimide, Estramustine, Medroxyprogesteroneacetate, Leuprolide, Flutamide, Toremifene, Zoladex can also be administered to the patient.

Also suitable for use in the combination chemotherapeutic methods of the invention are antiangiogenics such as matrix metalloproteinase inhibitors, and other VEGF inhibitors, such as anti-VEGF antibodies and small molecules such as ZD6474 and SU6668 are also included. Anti-Her2 antibodies from Genetech may also be utilized. A suitable EGFR inhibitor is EKB-569 (an irreversible inhibitor). Also included are Imclone antibody C225 immunospecific for the EGFR, and src inhibitors.

Also suitable for use as an antiproliferative cytostatic agent is Casodex™ which renders androgen-dependent carcinomas non-proliferative. Yet another example of a cytostatic agent is the antiestrogen Tamoxifen which inhibits the proliferation or growth of estrogen dependent breast cancer. Inhibitors of the transduction of cellular proliferative signals are cytostatic agents. Examples are epidermal growth factor inhibitors, Her-2 inhibitors, MEK-1 kinase inhibitors, MAPK kinase inhibitors, P13 inhibitors, Src kinase inhibitors, and PDGF inhibitors.

As mentioned, certain anti-proliferative agents are anti-arigiogenic and antivascular agents and, by interrupting blood flow to solid tumors, render cancer cells quiescent by depriving them of nutrition. Castration, which also renders androgen dependent carcinomas non-proliferative, may also be utilized. Starvation by means other than surgical disruption of blood flow is another example of a cytostatic agent. A particular class of antivascular cytostatic agents is the combretastatins. Other exemplary cytostatic agents include MET kinase inhibitors, MAP kinase inhibitors, inhibitors of non-receptor and receptor tyrosine kinases, inhibitors of integrin signaling, and inhibitors of insulin-like growth factor receptors.

Also suitable are anthracyclines (e.g., daunorubicin, doxorubicin), cytarabine (ara-C; Cytosar-U®); 6-thioguanine (Tabloid®), mitoxantrone (Novantrone®) and etoposide (Ve-Pesid®), amsacrine (AMSA), and all-trans retinoic acid (ATRA).

The compounds of the present invention may be useful in combination with BCR-ABL inhibitors such as, but not limited to, Gleevec® (imatinib, STI-571) or AM-107.

The compounds of the present invention may be useful in combination with anti-cancer compounds such as fentanyl, doxorubicin, interferon alfa-n3, palonosetron dolasetron anastrozole, exemestane, bevacizumab, bicalutamide, cisplatin, dacarbazine, cytarabine, clonidine, epirubicin, levamisole, toremifene, fulvestrant, letrozole, tamsulosin, gallium nitrate, trastuzumab, altretamine, hydroxycarbamide, ifosfamide, interferon alfacon-1, gefitinib, granisetron, leuprorelin, dronabinol, megestrol, pethidine, promethazine, morphine, vinorelbine, pegfilgrastim, filgrastim, nilutamide, thiethylperazine, leuprorelin, pegaspargase, muromonab-CD3, porfimer sodium, cisplatin, abarelix, capromab, samarium SM153 lexidronam, paclitaxel, docetaxel, etoposide, triptorelin, valrubicin, nofetumomab merpentan technetium 99m Tc, vincristine, capecitabine, strptozocin, and ondansetron.

Thus, another embodiment of the present invention is to provide methods for the treatment of a variety of cancers, including, but not limited to, the following:

carcinoma including that of the bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, and skin (including squamous cell carcinoma);

hematopoietic tumors of lymphoid lineage including leukemia, acute lymphocytic leukemia, acute lymphoblastic leukemia, B-cell lymphoma, T-cell lymphoma, Hodgkin's lymphoma, non-Hodgkin's lymphoma, hairy cell lymphoma, histiocytic lymphoma, and Burketts lymphoma;

hematopoietic tumors of myeloid lineage including acute and chronic myelogenous leukemias, myelodysplastic syndrome, myeloid leukemia, and promyelocytic leukemia;

tumors of the central and peripheral nervous system including astrocytoma, neuroblastoma, glioma, and schwannomas;

tumors of mesenchymal origin including fibrosarcoma, rhabdomyoscarcoma, and osteosarcoma; and other tumors including melanoma, xenoderma pigmentosum, keratoactanthoma, seminoma, thyroid follicular cancer, and teratocarcinoma.

Another embodiment of the present invention is to provide methods for the treatment of a variety of non-cancerous proliferative diseases. The invention is used to treat GIST, Breast cancer, pancreatic cancer, colon cancer, NSCLC, CML, and ALL, sarcoma, and various pediatric cancers.

The metabolites of the compound of formula (I) may be useful in combination with the compound of formula (I) or in combination with one of the other metabolites of the compound of formula (I).

The compounds of the present invention are protein tyrosine kinase inhibitors and as such are useful in the treatment of immunological disorders in addition to oncological disorders. U.S. Pat. No. 6,596,746 describes the utility of the compound in immunological disorders and is hereby incorporated by reference for the description of the compound in such immunological disorders.

Another embodiment of the present invention is a pharmaceutical composition useful in the treatment of cancer, comprising the administration of a therapeutically effective amount of the compounds of the present invention, with or without pharmaceutically acceptable carriers or diluents. The compositions of the present invention may further comprise one or more pharmaceutically acceptable additional ingredient(s) such as alum, stabilizers, antimicrobial agents, buffers, coloring agents, flavoring agents, adjuvants, and the like. The compounds of the present invention and compositions of the present invention may be administered orally or parenterally including the intravenous, intramuscular, intraperitoneal, subcutaneous, rectal and topical routes of administration.

Another embodiment of the present invention is a pharmaceutical composition useful in the treatment of cancer, comprising the administration of a therapeutically effective amount of the combinations of this invention, with or without pharmaceutically acceptable carriers or diluents. The pharmaceutical compositions of this invention comprise an antiproliferative agent or agents, a compound(s) of the present invention, and a pharmaceutically acceptable carrier. The methods entail the use of a neoplastic agent in combination with a compound of the present invention. The compositions of the present invention may further comprise one or more pharmaceutically acceptable additional ingredient(s) such as alum, stabilizers, antimicrobial agents, buffers, coloring agents, flavoring agents, adjuvants, and the like. The antineoplastic agents, compounds of the present invention, compounds and compositions of the present invention may be administered orally or parenterally including the intravenous, intramuscular, intraperitoneal, subcutaneous, rectal and topical routes of administration.

Another embodiment of the present invention also provides using the compounds obtained with the inventive process to further prepare pharmaceutical compositions capable of treating Src-kinase associated conditions, including the conditions described above. The said compositions may contain other therapeutic agents. Pharmaceutical compositions may be formulated by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulations.

The said pharmaceutical compositions may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds of the present invention may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds of the present invention, prepared according to the inventive process, may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The compounds of the present invention may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of the present invention may be determined by one of ordinary skill in the art, and includes exemplary dosage amounts for a mammal of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of Src kinase levels.

Compounds of the present invention may be tested for activity as inhibitors of protein kinases using one or more of the assays described below, or variations thereof that are within the level ordinary skill in the art.

Kinase Assays

SRC Kinase

The biochemical kinase assay to quantitate the inhibition of kinase activity by kinase inhibitors were performed in vitro in 96-well microtiter plates. All kinase inhibitors were dissolved in 100% DMSO and diluted into 2× the final concentration with PBS/1% DMSO prior to assay. Kinase reaction consisted of 5 ng of baculovirus expressed GST-SRC, 1.5 mM poly(Glu/Tyr) (Sigma), 0.3 mM ATP, and 0.15 mCi [g-33P] ATP in 50 ml kinase buffer (50 mM Tris, pH 7.4, 2 mM dithiothreitol (DTT), 0.1 mg/ml BSA, 0.3 mM MnCl2). The reaction mixture was incubated at 28° C. for 1 hour. The reaction was terminated by adding 10 ml of stopping buffer consisting of 2.5 mg/ml BSA and 300 mM EDTA followed by immediate precipitation with 110 ml of 10% TCA on ice for 30 min. The precipitates were transferred to a 96-well Uni-Filter GF/C plate. The amount of the phosphorylated synthetic substrate was quantitated using a TopCount 96-well liquid scintillation counter (PerkinElmer Life Sciences Inc, Boston, Mass.). Dose-response curves were generated to determine the concentration of the inhibitors required to inhibit 50% of kinase activity (IC50). IC50 values were derived by non-linear regression analysis and have a coefficient of variance=16% (SD/mean, n=3). The reported IC50 value was the average from at least three separate experiments.

LCK Kinase

The same procedure as that of SRC kinase detailed above was applied to the LCK kinase assay, except that the reaction consisted of 20 ng baculovirus expressed GST-LCK protein.

YES Kinase

The same procedure as that of SRC kinase detailed above was applied to the YES kinase assay, except that the reaction consisted of 10 ng baculovirus expressed GST-YES protein.

FYN Kinase

The same procedure as that of SRC kinase detailed above was applied to the LCK kinase assay, except that the reaction consisted of 20 ng baculovirus expressed GST-FYN protein.

BCR-ABL Kinase

The same procedure as that of SRC kinase detailed above was applied to the BCR-ABL kinase assay, except that the reaction consisted of 250 ng baculovirus expressed GST-BCR-ABL protein.

c-KIT Kinase

The biochemical assay to determine inhibition of c-KIT kinase activity was performed as described in section 3.1.2.1, with the exception that each reaction mixture contained 250 ng of recombinant GST-c-KIT protein purified from Sf9 insect cells. The GST-c-KIT protein contains the entire cytoplasmic sequence of c-KIT. The mixture contained also 1.5 mM poly (Glu/Tyr) (Sigma), 1 M ATP, and 0.15 mCi[g-$^{33}$P]ATP in 50 ml kinase buffer (50 mM Tris, pH 7.7, 2 mM DTT, 0.1 mg/ml BSA, 5 mM MgCl$_2$). Incorporation of radioactive phosphate and the determination of IC50 values were also carried out as described above.

PDGF Receptor Kinase

The PDGFR-b human receptor tyrosine kinase was assayed using the synthetic polymer poly(Glu4/Tyr) (Sigma Chemicals) as a phosphoacceptor substrate. Each reaction mixture consisted of a total volume of 50 ml and contained 200 ng of baculovirus expressed enzyme, 64 mg/ml poly (Glu4/Tyr), 3.6 mM of ATP, and 0.7 mCi of [g-$^{33}$P]ATP. The mixture also contained 20 mM HEPES, pH 7.0, 5 mM MnCl$_2$, 150 mM NaCl, 0.5 mM DDT, and 25 mg/ml bovine serum albumin (BSA). The reaction mixtures were incubated at 27° C. for 60 minutes and kinase activity was determined by quantitation of the amount of radioactive phosphate transferred to the poly(Glu4/Tyr) substrate. Incorporation was measured by the addition of cold trichloroacetic acid. Precipitates were collected onto GF/C UniFilter plates (Packard Instrument Co., Meriden, Conn.) using a Filtermate universal harvester and quantitated using a TopCount 96-well liquid scintillation counter (Packard Instrument Co., Meriden, Conn.). Compounds were dissolved in dimethylsulfoxide (DMSO) to a concentration of 10 mM and were evaluated at six concentrations diluted four-fold, each in triplicate. The final concentration of DMSO in the kinase assays was 0.5%, which was shown to have no effect on kinase activity. IC50 values were derived by non-linear regression analysis and have a coefficient of variance (SD/mean, n=6)=10%.

EPHA2 Receptor Kinase

The biochemical assay to determine inhibition of EPHA2 kinase activity was performed as described above, with the exception that each reaction mixture contained 100 ng of recombinant GST-EPHA2 protein purified from Sf9 insect cells. The GST-EphA2 protein consists of the entire cytoplasmic sequence of EPHA2 fused to the c-terminus of GST. The mixture contained also 1.5 mM poly (Glu/Tyr) (Sigma), 1 mM ATP, and 0.15 mCi[g-$^{33}$P]ATP in 50 ml kinase buffer (50 mM Tris, pH 7.7, 2 mM DTT, 0.1 mg/ml BSA, 5 mM MgCl2). Incorporation of radioactive phosphate and the determination of IC50 values were also carried out as described above.

Methods of Preparation

EXAMPLE 1

Preparation of the Compound of Formula (II):

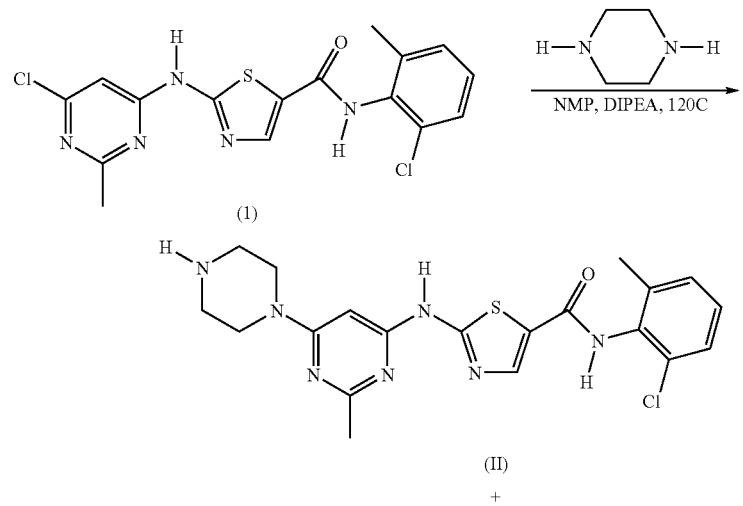

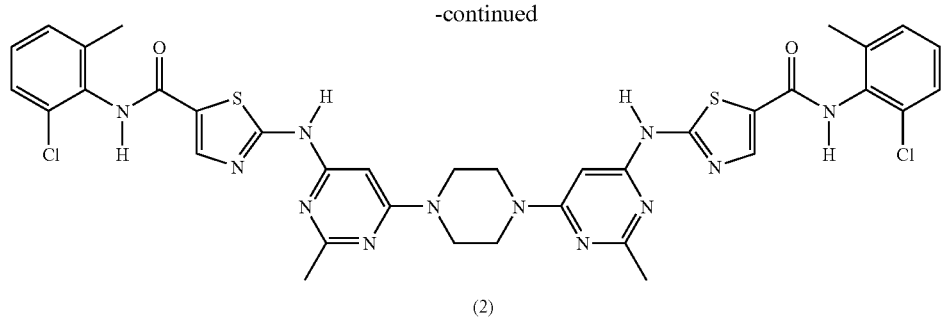

(2)

In a 50 mL round bottomed flask equipped with a magnetic stirrer, condenser, Ar inlet, temperature controller (J-Kem) and heating mantle was introduced compound (1) (1.0 g, 2.53 mmoles, HPLC 95.28%), N-methylpyrrolidone (6.5 mL), piperazine (0.26 g, 3.043 mmoles, 1.2 eqs) and diisopropylethylamine (0.88 mL, 5.072 mmoles, 2 eqs). The suspension was heated at 120° C. for 45 min (HPLC showed 56.3% (II), 21.1% (2) and 0.6% of starting (1)). The mixture was cooled at r.t. and diluted slowly with water (27.8 mL) to precipitate the product. The solid was collected by filtration and rinsed with water (14 mL). The solid collected showed only 45.2% of (II) along with 31.4% (2)). A white solid also crystallized out of the filtrate. The material was collected by filtration and dried under high vacuum at 40° C. for 16 hrs to give 0.22 g (0.49 mmole, 19.6% yield) of (II) as a white solid (HPLC 86.9%).

HPLC system.
Column; Luna C-18, 4.6×75 mm, 3 u
Mobile phase A; 100% $H_2O$+0.05% TFA
Mobile phase B; 100% $CH_3CN$+0.05% TFA
Gradient; 1% B to 95% B in 15 min, hold 95% B for 2 min
Flow Rate; 1 mL/min
Inj. Volume; 5 uL
Detection; 255 nm
Column temperature; 25° C.
Retention times; (II) (7.04 min), (2) (9.70 min), (1) (10.73 min).
1H NMR (400 MHz, DMSO-d6) δ 9.85 (s, 1H), 8.20 (s, 1H), 7.39 (d, 1H, Ph, J=7.6 Hz), 7.28 (d, 1H, Ph, J=7.1 Hz), 7.24 (t, 1H, Ph, J=7.7 Hz), 6.01 (s, 1H), 3.43 (m, 4H, piperazine), 2.73 (m, 4H, piperazine), 2.39 (s, 3H, $CH_3$), 2.23 (s, 3H, $CH_3$) $ES^+$ MS m/z (rel. intensity) 444 ($MH^+$, 100)

Preparation of the Compound of Formula (III):

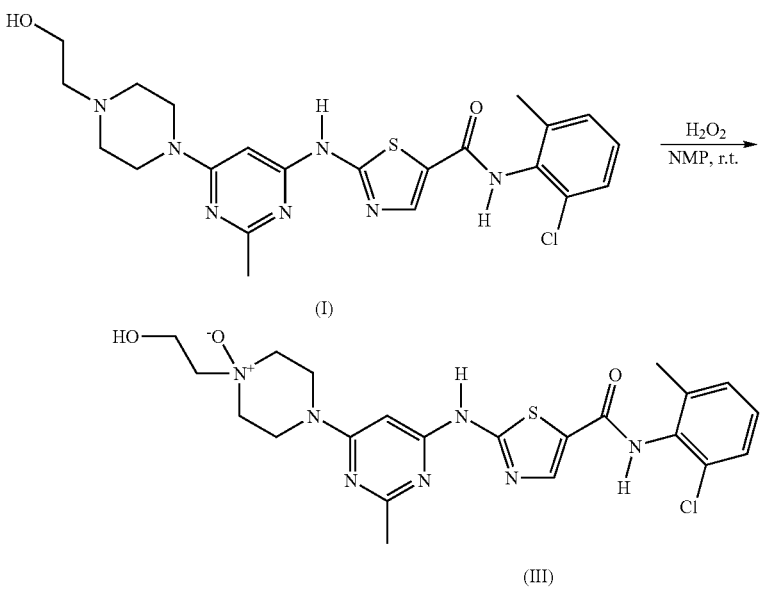

In a 50 mL round bottomed flask equipped with a magnetic stirrer was introduced the compound of formula (I) (0.41 g, 0.84 mmole) and 3.0 mL of N-methylpyrrolidone. The solution was treated with aq. $H_2O_2$ (35% soln, 3.0 mL, 30.8 mmoles, 36.7 eqs.) and stirring pursued at r.t. for ca 18 hrs. HPLC after 18 hr showed 98.26% product and 1.73% s.m. The reaction was stopped at this point and combined with earlier run (0.5 g run).

The white solid was collected by filtration and rinsed with 2×5 mL water. The solid was dried at 40° C. under high vacuum for 18 hrs to give 1.08 g (2.14 mmoles, >100% yield, contaminated with NMP) of (III) with HPLC 99.66%.

HPLC system; same as described above in the preparation of (II)

Retention time; (I); 7.13 min, (III); 7.41 min

1H NMR (400 MHz, DMSO-d6) δ 9.88 (s, 1H), 8.22 (s, 1H), 7.39 (dd, 1H, J=7.8 and 1.4 Hz, Ph), 7.28 (dd, 1H, J=7.4 and 1.0 Hz, Ph), 7.24 (t, 1H, J=7.6 Hz, Ph), 4.34 (bs, 1H, OH), 4.10 (bd, 2H, J=12.4 Hz, $CH_2$), 3.91 (m, 2H, $CH_2$), 3.64 (t, 2H, J=12.4 Hz, $CH_2$ piperazine) 3.35 (m, 6H, $CH_2$ piperazine), 2.42 (s, 3H, $CH_3$), 2.23 (s, 3H, $CH_3$). ES+ MS m/z (rel. intensity) 504 (MH+, 100).

Preparation of Compound (IV):

Ethyl 2-(4-(6-(5-((2-chloro-6-methylphenyl)carbamoyl)thiazol-2-ylamino)-2-methylpyrimidin-4-yl)piperazin-1-yl)acetate (IV)

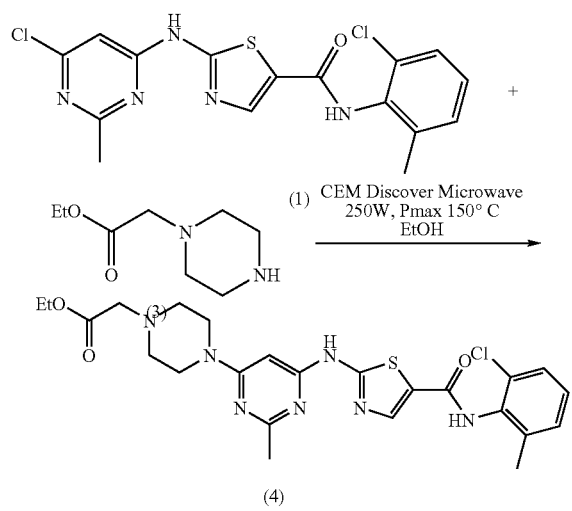

A mixture of 2-(6-chloro-2-methylpyrimidin-4-ylamino)-N-(2-chloro-6-methylphenyl)thiazole-5-carboxamide (1) (0.20 g, 0.51 mmol) and 1-(ethoxycarbonylmethyl)piperazine (3) (0.17 g, 1.01 mmol) in 4 mL of EtOH was heated with a CEM Discover® microwave at 250 W, Pmax 150° C. for 45 min. The resulting mixture was treated with EtOH (6 mL) and then stirred at rt for 1 h. The solid was collected on a filter to give 0.24 g of ethyl 2-(4-(6-(5-((2-chloro-6-methylphenyl)carbamoyl)thiazol-2-ylamino)-2-methylpyrimidin-4-yl)piperazin-1-yl)acetate (4) (89% yield). HPLC>99% pure (Rt 2.517 min); LC/MS (ES+) 530/532 (M+H, 100); 1H NMR (DMSO-d6) δ 11.48 (s, 1H), 9.86 (s, 1H), 8.22 (s, 1H), 7.40 (m, 1H), 7.28 (m, 2H), 6.06 (s, 1H), 4.10 (q, J=7.1 Hz, 2H), 3.53 (s, 4H ??), 3.29 (s, 2H), 2.59 (t, J=4.6 Hz, 4H), 2.41 (s, 3H), 2.24 (s, 3H), 1.20 (t, J=7.1 Hz, 3H); Anal. Calcd for $C_{24}H_{28}ClN_7O_3S$: C, 54.38; H, 5.32; Cl, 6.69; N, 18.50; S, 6.05. Found: C, 54.24; H, 5.16; Cl, 6.80; N, 18.59; S, 6.09.

HPLC conditions column: YMC ODS-A S5 4.6×50 mm; UV: 220 nm; gradient time: 4 min; flow rate: 4 mL/min, 0-100% B; solvent A: 10% MeOH/90% $H_2O$ with 0.2% $H_3PO_4$, solvent B: 90% MeOH/10% $H_2O$ with 0.2% $H_3PO_4$.

2-(4-(6-(5-((2-Chloro-6-methylphenyl)carbamoyl) thiazol-2-ylamino)-2-methylpyrimidin-4-yl)piperazin-1-yl)acetic acid (IV)

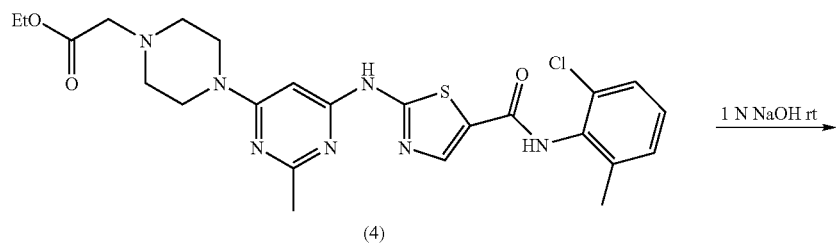

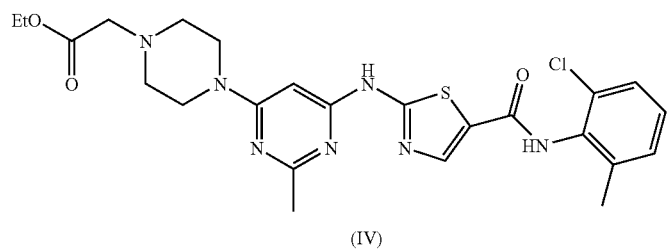

A mixture of ethyl 2-(4-(6-(5-((2-chloro-6-methylphenyl)carbamoyl)thiazol-2-ylamino)-2-methylpyrimidin-4-yl)piperazin-1-yl)acetate (4) (0.21 g, 0.40 mmol) in 10 mL of MeOH was added 1.0 N NaOH (2.4 mL, 2.4 mmol) at rt. The mixture was stirred at rt for 1 h to become a clear solution. The HPLC indicated the reaction was complete with a single peak with Rt 2.417 min. The solvents in the solution were reduced to a small volume. The remaining liquid was treated with $H_2O$ (10 mL). The aqueous solution was washed with $CH_2Cl_2$ (2×10 mL) and then adjusted to pH 6-7 with 1 N HCl (2.4 mL) to result in white precipitation. The solid was collected on a filter, washed with water to give 0.18 g of 2-(4-(6-(5-((2-chloro-6-methylphenyl)carbamoyl)thiazol-2-ylamino)-2-methylpyrimidin-4-yl)piperazin-1-yl)acetic acid (IV) (90% yield). HPLC>99% pure. LC/MS (ES$^+$) 502/504 (M+H, 100), HRMS calcd for $C_{22}H_{24}ClN_7O_3S$ 502.1428, found 502.1413.1H NMR (DMSO-d6) δ 11.49 (br s, 1H), 9.89 (s, 1H), 8.23 (s, 1H), 7.41(dd, J=7.5, 1.6 Hz, 1H), 7.28 (m, 2H), 6.07 (s, 1H), 3.55 (s, 4H0, 3.19 (s, 2H), 2.61 (t, J=4.7 Hz, 4H), 2.42 (s, 3H), 2.24 (s, 3H). Anal. Calcd for $C_{22}H_{24}ClN_7O_3S$ 0.85$H_2O$: C, 51.08; H, 5.01; Cl, 6.85; N, 18.95; S, 6.20; $H_2O$, 2.96%. Found: C, 51.23; H, 4.97; Cl, 7.08; N, 19.09; S, 5.92; $H_2O$, 2.94%.

Preparation of Compounds (V) and (VI):

The compounds of formula (V) and (VI) corresponding to metabolites M20 and M24, respectively, were biosynthesized in 100-mL incubations with HLM (compound (I): 0.1 mM; protein: 2 mg/ml; NADPH: 5 mM; $MgCl_2$: 2.5 mM; methanol: 5% v/v; potassium phosphate: 0.1 M. pH 7.4, 37° C., 90 min). The reaction was stopped by adding an equal volume of cold ACN. After removal of the protein pellet by centrifugation, solvent was evaporated to give a white residue, which were then dissolved in methanol and were purified using a Shimazu semi-prep HPLC system with the following conditions: column, YMC ODS AQ 20×150 mm, S5; mobile phase, 0.1% formic acid in water (A)/0.1% formic acid in acetonitrile (B); gradient, 5% to 15% B in 5 min, 15% B at 31 min; flow rate, 10 ml/min. Fractions containing compound (V) (M20), and compound (VI) (M24), were pooled separately and lyophilized. Approximately 1.5 mg of compound (V) and 0.3 mg of compound (VI) were isolated as their formic acid salts. The metabolite samples were dissolved in $d_6$-DMSO or $D_2O/CD_3OD$ and analyzed using a Bruker 700 MHz NMR equipped with a cryo probe. NMR spectra for compound (V) and (VI) are shown in Tables 17 and 18, respectively.

TABLE 17

Key NMR data for compound (V) (M20) (C-13 chemical shift data were obtained from HMBC)* compound (V) (M20)

| Position | $^1$H ppm (mult, J (Hz)) | $^{13}$C ppm | HMBC ($^1$H-$^{13}$C correlation) |
|---|---|---|---|
| 23 | n/a | 125 | |
| 24 | n/a | 133 | |
| 25 | 6.77 (d, (2.65)) | 113.8 | C23, C24, C26, C27 |
| 26 | n/a | 157 | |

TABLE 17-continued

Key NMR data for compound (V) (M20) (C-13 chemical shift data were obtained from HMBC)* compound (V) (M20)

| Position | $^1$H ppm (mult, J (Hz)) | $^{13}$C ppm | HMBC ($^1$H-$^{13}$C correlation) |
|---|---|---|---|
| 27 | 6.67 (d, (2.65)) | 116.3 | C23, C25, C26 |
| 28 | n/a | 139 | |
| 33 | 2.14 (s) | 18.8 | C23, C27, C28 |

*Only key proton and carbon chemical shifts that helped in the identifying the site of hydroxylation are shown.

TABLE 18

Key proton NMR data for compound (VI) (M24*)

compound (VI) (M24)

| Position | $^1$H ppm |
|---|---|
| 25 | 7.42 (d, J = 8.0 Hz) |
| 26 | 7.35 (t, J = 8.0 Hz) |
| 27 | 7.46 (d, J = 8.0 Hz) |
| 33 | 4.54 (s) |

*Only key proton chemical shifts that helped in the identifying the site of hydroxylation are shown.

Microbial Biosynthesis of Compound (V) (M20) and (VI) (M24):

Due to limitations in the ability to scale up HLM incubations, microbial biotransformation was employed to generate larger quantities of both metabolites. Screening with a microbial screening plate (containing 21 actinomycetes strains) indicated that six strains were capable of producing both compound (V) and compound (VI) from compound (I). Two strains, *Streptomyces* sp. SC15761 and *Streptomyces* sp. SC2417, seemed to give higher yield than the other strains. Thus reactions with both strains were scaled up for isolation of compound (V) and compound (VI).

A frozen vial (approximately 2 mL) of *Streptomyces* sp. strain SC15761 was used to inoculate a 500 mL flask containing 100 mL of malt extract broth, which consisted of 20 g of dextrose, 10 g of malt extract, 10 g of yeast extract and 1 g of peptone in one liter of deionized water (pH was adjusted to 7 before sterilization at 120° C. for 20 minutes). The vegetative culture was incubated for three days at 28° C. on a rotary shaker operating at 250 rpm. One mL of the resulting culture was added to each of eleven 500 mL flasks containing 100 mL of the malt extract broth. The cultures were incubated at 28° C. and 250 rpm for 24 hours. Compound (I) in DMSO (200 μl of a 48.9 mg/mL solution) was added to each of eleven flasks. The flasks were then returned to the shaker and incubated for an additional 27 hours at 28° C. and 250 rpm. The reaction culture was then processed for the recovery of compounds (V) and (VI).

A frozen vial (approximately 2 mL) of *Streptomyces* sp. strain SC2417 was used to inoculate a 500 mL flask containing 100 mL of malt extract broth, which consists of 20 g of dextrose, 10 g of malt extract, 10 g of yeast extract and 1 g of peptone in one liter of deionized water (pH was adjusted to 7 before sterilization at 120° C. for 20 minutes). The vegetative culture was incubated for three days at 28° C. on a rotary shaker operating at 250 rpm. One mL of the resulting culture was added to each of eleven 500 mL flasks containing 100 mL of the malt extract broth. The cultures were incubated at 28° C. and 250 rpm for 24 hours. Two hundred micro liter of compound (I) solution in DMSO (48.9 mg/mL) was added to each of eleven flasks. The flasks were then returned to the shaker and incubated for an additional 48 hours at 28° C. and 250 rpm. The reaction culture was then processed for the recovery of compounds (V) and (VI).

The biotransformation cultures from *Streptomyces* sp. strain SC15761 were pooled and extracted twice with 1000 mL and 500 mL of ethyl acetate, respectively. The combined ethyl acetate extract was evaporated to dryness. The residue was dissolved in 2 mL of DMSO and subjected to preparative HPLC.

The biotransformation cultures from *Streptomyces* sp. strain SC2417 were pooled and extracted with 1000 mL ethyl acetate. The ethyl acetate extract was evaporated to dryness. The residue was dissolved in 1.3 mL of DMSO and subjected to preparative HPLC.

Two preparative HPLC systems were used in combination to achieve purification of compound (V) and (VI). System 1 used a YMC ODS-AQ (30 mm ID×150 mm length, S-10) column, a gradient of two solvents (solvent A: 0.1% formic acid in water and solvent B: 0.1% formic acid in acetonitrile) with 10% to 20% B in 3 min, 20% B for 22 min, and an elution flow rate of 20 mL/min. System 2 used a YMC ProC18 (20 mm ID×250 mm length, S-5) column, a gradient of two solvents (solvent A: 0.1% formic acid in water and solvent B: methanol) with 15% to 27% B in 3 min, 27% B for 45 min, and an elution flow rate of 10 mL/min. Fractions containing compounds (V) and (VI) were pooled and lyophilized. Approximately 5 mg of compound (V) and 4 mg of compound (VI) were isolated as their formic acid salts.

The reaction and purification were monitored by analytical HPLC with a Hewlett Packard 1100 Series Liquid Chromatograph using an YMC ProC18 column, 4.6 mm i.d.×15 cm 1 S5. A gradient system of 0.1% formic acid in water (solvent A) and methanol (solvent B) was used: 20% to 30% B linear gradient for 1 min, 30% B for 10 min, and 30% to 80% linear gradient for 1 min. The flow rate was 1 mL/min and UV detection was at 320 nm. Retention times for compound (V) and (VI) were 8.0 and 10.0 min, respectively (retention times were affected by composition of sample solvents, but elution order remained the same).

Co-injection of the compound (V) purified from the microbial biotransformation reaction and the metabolite M20 previously isolated from a HLM incubation onto the analytical HPLC and gave a single peak at 8.0 min. The peak area of the mixture matched the sums of the peak areas of the two samples when they were injected individually.

Co-injection of compound (VI) purified from the microbial biotransformation reaction and the metabolite M24 previously isolated from a HLM incubation onto the analytical HPLC and gave a single peak at 10.0 min. The peak area of the mixture matched the sums of the peak areas of the two samples when they were injected individually.

LC/MS analysis of M20: +ESI [M+H$^+$]: m/z 504; MS2: m/z 504→m/z 417; MS3: m/z 504→m/z 417→m/z 381, 232, 260.

LC/MS analysis of M24: +ESI [M+H$^+$]: m/z 504; MS2: m/z 504→m/z 486, 347; MS3: m/z 504→m/z 486→m/z 399, 347, 263.

The above MS/MS fragmentation patterns were the same as those obtained with the corresponding metabolites previously isolated from human liver microsome incubations.

For NMR analysis, the metabolite samples were dissolved in DMSO-$d_6$ and analyzed by Inova 500 MHZ NMR or a Bruker 700 MHz NMR equipped with a cryo probe. The chemical shift was referenced to DMSO-d6 (proton, δ 2.50 ppm; C-13, δ 39.5 ppm), and $^{13}$C chemical shift data were deduced from HMBC and HMQC spectra. The peak assignment was based on HMBC and HMQC analysis (using the same numbering as for Tables 17 and 18 above).

| Key NMR data for compound (V) (formic acid salt) | | |
|---|---|---|
| | $^1$H | |
| Position | ppm(mult, J(Hz)) | $^{13}$C ppm |
| 23 | n/a | 125.34 |
| 24 | n/a | 132.99 |
| 25 | 6.77 (d, (2.58)) | 113.95 |
| 26 | n/a | 157.04 |
| 27 | 6.68 (d, (2.58)) | 115.83 |
| 28 | n/a | 139.60 |
| 33 | 2.13(s) | 19.24 |

| Key NMR data for compound (VI) (formic acid salt) | | |
|---|---|---|
| | $^1$H | |
| Position | ppm(mult, J(Hz)) | $^{13}$C ppm |
| 23 | n/a | 131.38 |
| 24 | n/a | 132.56 |
| 25 | 7.46 (d, (7.8)) | 127.77 |
| 26 | 7.37(t, (7.8)) | 128.32 |
| 27 | 7.52 (d, (7.8)) | 125.72 |
| 28 | n/a | 143.65 |
| 33 | 4.48(s) | 59.8 |

Preparation of N-(2-chloro-6-(hydroxymethyl)phenyl)-2-(6-(4-(2-hydroxyethyl)piperazin-1-yl)-2-methylpyrimidin-4-ylamino)thiazole-5-carboxamide (VI)
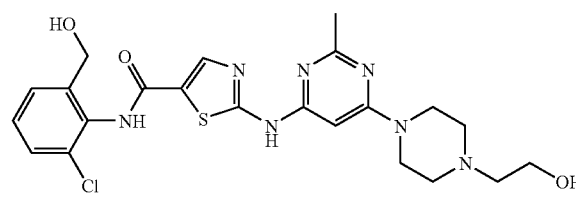
VI
The title compound was prepared according to the following reaction scheme:
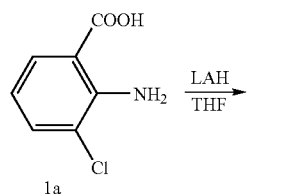
1a
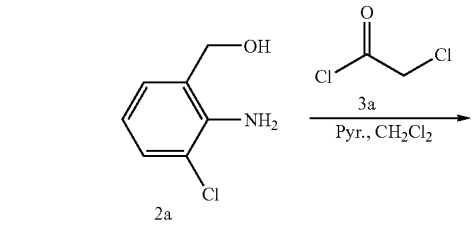
2a
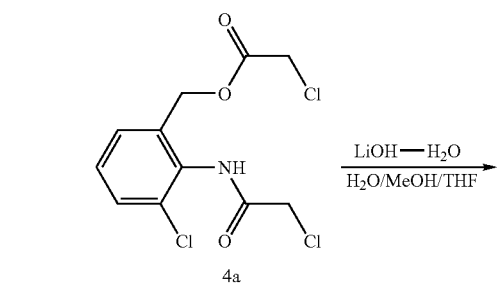
4a
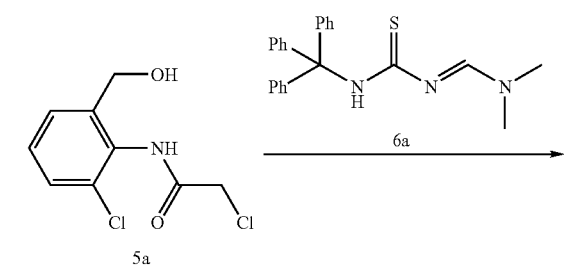
5a
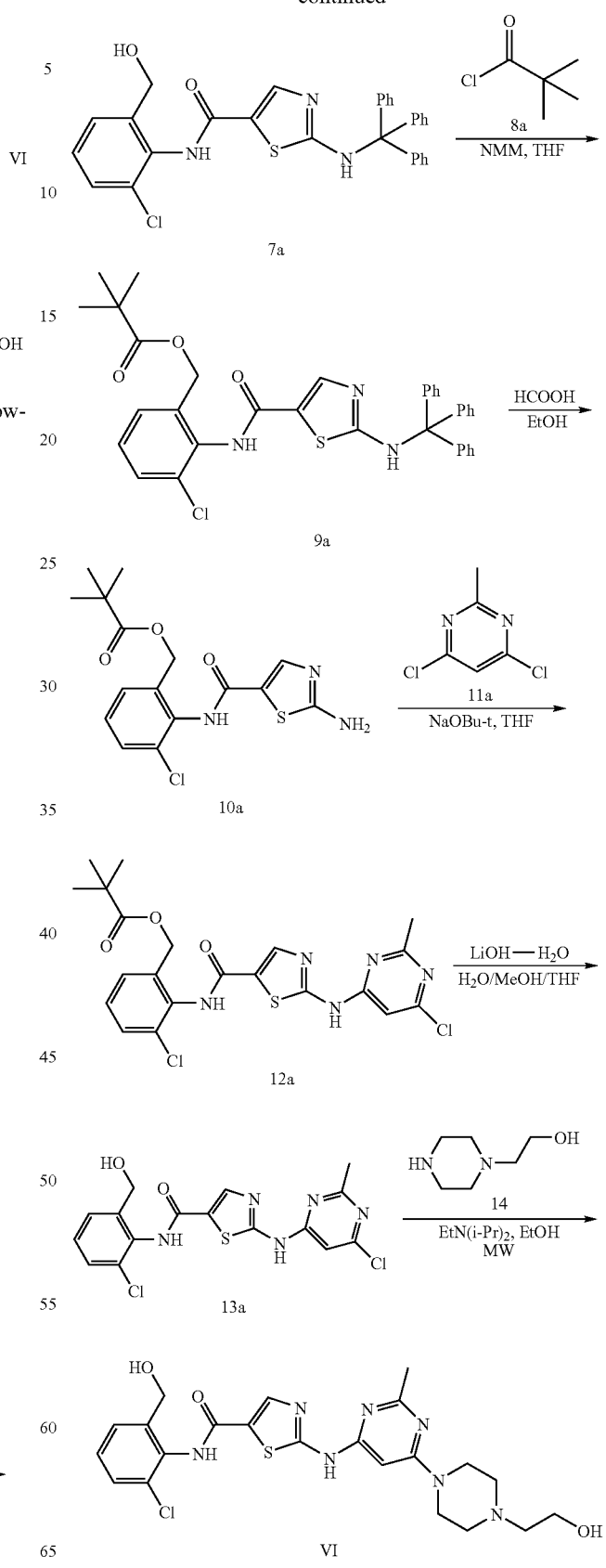

A. Preparation of compound (2-amino-3-chlorophenyl)methanol (2a)

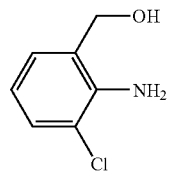

2a

To a solution of lithium aluminum hydride in THF (210 mL, 1 M, 210 mmol) at room temperature, under $N_2$, was added slowly a solution of compound 1a (15.0 g, 87.4 mmol) in THF (200 mL) over a period of 20 mins. The reaction mixture was stirred for another 1.5 h at room temperature before it was cooled to 10° C. Water (300 mL) was added slowly. The resulting suspension was filtered through a celite pad. The celite pad was rinsed with EtOAc (1 L). The filtrate was washed with brine (3×300 mL), dried over $Na_2SO_4$, filtered and concentrated in vacuo to give the product 2a (13.0 g, 94% yield). $^1$H NMR (500 MHz, CDCl$_3$) δ 4.69 (s, J=5.0 Hz, 1H), 6.63 (t, J=5.2 Hz, 1H), 6.97 (d, J=5.0, 1H), 7.24 (d, J=5.0 Hz, 1H).

B. Preparation of compound 3-chloro-2-(2-chloroacetamido)benzyl 2-chloroacetate (4a)

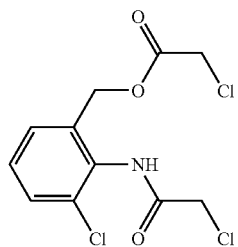

4a

Compound 2a (13.0 g, 82.5 mmol) was dissolved in $CH_2Cl_2$ (500 mL). The solution was cooled to −10° C. Pyridine (20 mL) was added followed by addition of chloroacetyl chloride (16.4 mL, 206.5 mmol). The reaction mixture was allowed to warm to 10° C. over a period of 2.5 h. It was then quenched with 1 N HCl (500 mL). The organic phase was separated. The aqueous layer was extracted with $CH_2Cl_2$ (300 mL). The combined organic extracts were washed with $H_2O$ (500 mL), brine (500 mL), dried over $MgSO_4$, filtered and concentrated in vacuo to give the crude product 3 which was recrystallized from 30% EtOAc in hexane to give the compound 4a (24.8 g, 97% yield). $^1$H NMR (500 MHz, CDCl$_3$) δ 4.08 (s, 2H), 4.26 (s, 2H), 5.19 (s, 2H), 7.30 (t, J=5.0 Hz, 1H), 7.38 (d, J=5.0 Hz, 1H), 7.48 (d, J=5.0 Hz, 1H); $^{13}$C (125 MHz, CDCl$_3$) δ 40.73, 42.75, 64.62, 128.33, 128.87, 130.34, 131.81, 132.18, 134.53, 165.11, 167.09; Anal. Calcd for $C_{11}H_{10}Cl_3NO_3$: C, 42.54; H, 3.24; N, 4.51. Found: C, 42.63; H, 3.19; N, 4.29.

C. Preparation of compound 2-chloro-N-(2-chloro-6-(hydroxymethyl)phenyl)acetamide (5a)

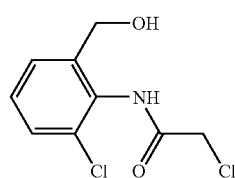

5a

Lithium hydroxide mono hydrate (12.55 g, 306 mmol) was dissolved in $H_2O$ (50 mL). To the solution was added MeOH (50 mL). The mixture was then cooled to −10° C. A solution of compound 4a (19.0 g, 61.2 mL) in THF (300 mL) was added. The reaction mixture was allowed to warm to 15° C. over a period of 4 h. A saturated $NH_4Cl$ solution (200 mL) and EtOAc (200 mL) were added. The organic phase was separated and the aqueous layer was extracted with EtOAc (200 mL). The combined organic extracts were washed with brine (2×200 mL), dried over $Na_2SO_4$, filtered and concentrated in vacuo to give the crude compound 4 which was crystallized from a mixture of EtOAc and hexane (1:4) to give the pure compound 5a as a off white needles (12.1 g, 85% yield). $^1$H NMR (500 MHz, CDCl$_3$) δ 2.96 (bs, 1H), 4.29 (s, 2H), 4.56 (s, 2H), 7.30 (t, J=5.0 Hz, 1H), 7.44 (t, J=5.0 Hz, 2H), 8.33 (bs, 1H); Anal. Calcd for $C_9H_9Cl_2NO_2$: C, 46.18; H, 3.87; N, 5.98. Found: C, 46.21; H, 3.72; N, 5.80.

D. Preparation of N-(2-chloro-6-(hydroxymethyl)phenyl)-2-(tritylamino)thiazole-5-carboxamide (7a)

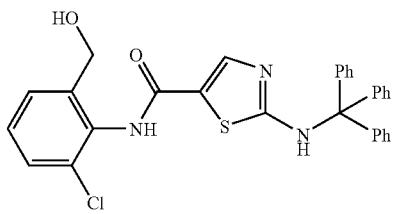

7a

A mixture of compound 5a (5.85 g, 25 mmol) and compound 6a (9.34 g, 25 mmol) in MeOH (50 mL) was heated to reflux for 22 h. The reaction mixture was then cooled to −10° C. The solid was filtered and washed with cold MeOH (2×10 mL). The filter cake was vacuum air dried overnight to give compound 7a (10.0 g, 76% yield). $^1$H NMR (500 MHz, DMSO) δ 4.40 (d, J=5.0 Hz, 2H), 5.23 (t, J=5.0 Hz, 1H), 7.22-7.48 (m, 18H), 7.69 (s, 1H), 9.18 (s, 1H), 9.56 (s, 1H).

E. Preparation of 3-chloro-2-(2-(tritylamino)thiazole-5-carboxamido)benzyl pivalate (9a)

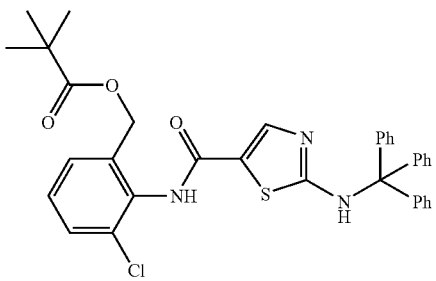

9a

To a solution of compound 7a (7.36 g, 14 mmol) in THF (200 mL) at 5° C. were added N-methylmorpholine (3.1 mL, 28 mmol) followed by slow addition of trimethylacetyl chloride (8a, 1.8 mL, 21 mmol). The reaction mixture was allowed to warm to room temperature over a period of 3 h. A solution of saturated NH$_4$Cl in H$_2$O (500 mL) was added. The mixture was extracted with EtOAc (2×250 mL). The combined extracts were washed with 1N HCl (500 mL), saturated NaHCO$_3$ (500 mL), dried over MgSO$_4$. The solution was filtered and concentrated in vacuo to give compound 9a as a white solid (8.90 g, 100% yield). $^1$H NMR (500 MHz, CDCl$_3$) δ 1.16 (s, 9H), 5.01 (s, 2H), 7.20-7.40 (m, 18H), 7.79 (s, 1H), 8.30 (bs, 1H).

F. Preparation of 2-(2-aminothiazole-5-carboxamido)-3-chlorobenzyl pivalate (10a)

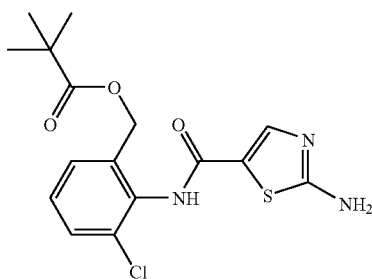

10a

A mixture of compound 9a (8.90 g, 14 mmol) and formic acid (15 mL, 96% in H$_2$O) in EtOH (150 mL) was refluxed for 24 h. After cooling, the solution was concentrated in vacuo. The residue was subjected to a short column using EtOAc in hexane (30% to 70%) to give the crude compound 10a which was triturated with 10% EtOAc in hexane to give compound 10a (4.50 g, 87% yield). $^1$H NMR (500 MHz, CDCl$_3$) δ 1.17 (s, 9H), 5.09 (s, 2H), 7.20-7.39 (m, 5H), 8.01 (s, 1H), 8.84 (s, 1H).

G. Preparation of 3-chloro-2-(2-(6-chloro-2-methylpyrimidin-4-ylamino)thiazole-5-carboxamido)benzyl pivalate (12a)

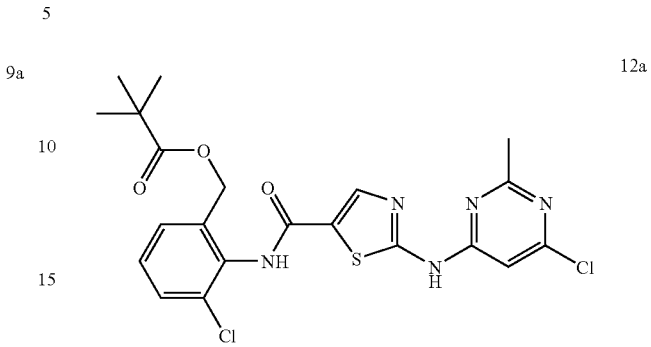

12a

To a solution of compound 10a (2.21 g, 6 mmol) and 4,6-dichloro-2-methylpyrimidine (11a, 1.18 g, 7.2 mmol) in THF (30 mL) was added a solution of NaOBu-t in THF (30% w/w, 7.4 mL) at temperature between 10° C. to 18° C. The reaction mixture was stirred at 18° C. for 1.5 h. It was then cooled to 0° C. A solution of 1N HCl (14.0 mL) was added. The mixture then was partitioned between EtOAc and H$_2$O (1:1, 200 mL). The organic phase was separated, and the aqueous layer was extracted with EtOAc (100 mL). The combined extracts were concentrated in vacuo. The residue was subjected to a flash column using 50% EtOAc in hexane to give crude compound 12a which was triturated with 10% EtOAc in hexane to give compound 12a (1.95 g, 66% yield). $^1$H NMR (500 MHz, CDCl$_3$) δ 1.19 (s, 9H), 2.73 (s, 3H), 5.12 (s, 2H), 6.93 (s, 1H), 7.21-7.49 (m, 3H), 8.21 (s, 1H), 8.98 (s, 1H).

H. Preparation of 2-(6-chloro-2-methylpyrimidin-4-ylamino)-N-(2-chloro-6-(hydroxymethyl)phenyl)thiazole-5-carboxamide (13a)

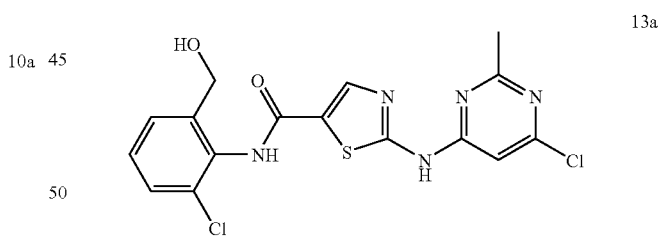

13a

To a solution of lithium hydroxide mono hydrate in H$_2$O (4 mL) were added MeOH (8 mL), compound 12a (1.93 g, 3.9 mmol) and THF (32 mL) respectively. The reaction mixture was stirred at room temperature for 6 h. To the reaction mixture was added a solution of 1N HCl (38 mL) to adjust the PH=7. H$_2$O (20 mL) was added. The mixture was stirred at room temperature for 30 mins. The precipitates were filtered and the filter cake was washed with H$_2$O (3×10 mL) and then vacuum air dried overnight. Compound 13a was collected as white solid (1.57 g, 98% yield). $^1$H NMR (500 MHz, DMSO-d$_6$) δ 2.60 (s, 3H), 4.50 (d, J=5.0 Hz, 2H), 5.31 (t, J=5.0 Hz, 1H), 6.96 (s, 1H), 7.39 (t, J=5.0 Hz, 1H), 7.47 (d, J=5.0 Hz, 1H), 7.53 (d, J=5.0 Hz, 1H), 8.31 (s, 1H), 9.95 (s, 1H), 12.24 (s, 1H).

EXAMPLE 1

Preparation of N-(2-chloro-6-(hydroxymethyl)phenyl)-2-(6-(4-(2-hydroxyethyl)piperazin-1-yl)-2-methylpyrimidin-4-ylamino)thiazole-5-carboxamide (VI)

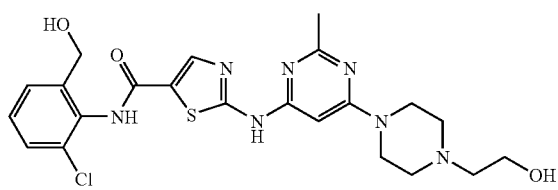

To a 20 mL microwave reaction tube was charged compound 13a (688 mg, 1.68 mmol), 2-hydroxyethylpiperizine (14, 437 mg, 3.36 mmol), ethyldiisopropylamine (434 mg, 3.36 mmol) and EtOH (10 mL). The mixture was heated at 110° C. for 1 h using a microwave reactor. The reaction mixture was then subjected to a short column using 0 to 10% 2M $NH_3$ in MeOH in $CH_2Cl_2$ as the eluent to give compound II as a white solid (504 mg, 60% yield). $^1$H NMR (500 MHz, MeOD) δ 2.49 (s, 3H), 2.59-2.64 (m, 6H), 3.66-3.68 (t, J=5.2 Hz, 4H), 3.75 (t, J=6.0 Hz, 2H), 4.68 (s, 2H), 6.03 (s, 1H); 7.39 (t, J=7.7 Hz, 1H), 7.47 (d, J=7.7 Hz, 1H), 7.56 (d, J=7.7 Hz, 1H), 8.17 (s, 1H); Anal. Calcd for $C_{22}H_{26}CN_7O_3S \cdot 0.57H_2O$: C, 51.38; H, 5.32; N, 19.07. Found: C, 51.16; H, 5.22; N, 18.97.

What is claimed is:

1. A substantially pure compound of formula (II),

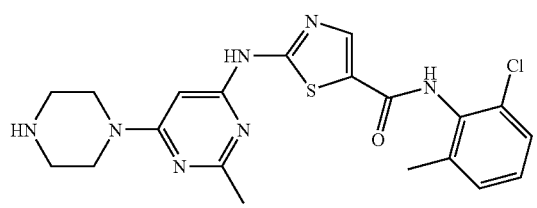

or a pharmaceutically acceptable salt form thereof.

2. A substantially pure compound of formula (III),

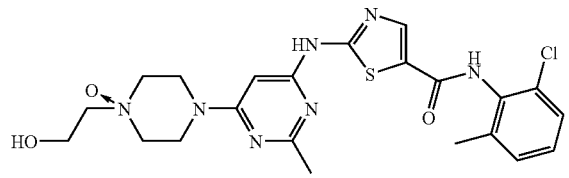

or a pharmaceutically acceptable salt form thereof.

3. A substantially pure compound of formula (IV),

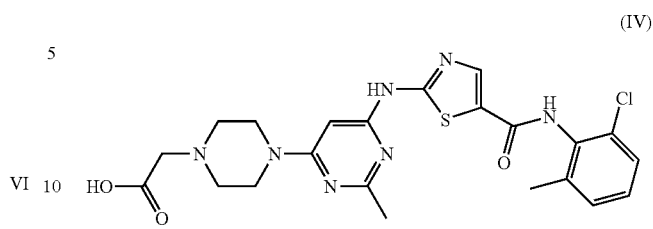

or a pharmaceutically acceptable salt form thereof.

4. A substantially pure compound of formula (V),

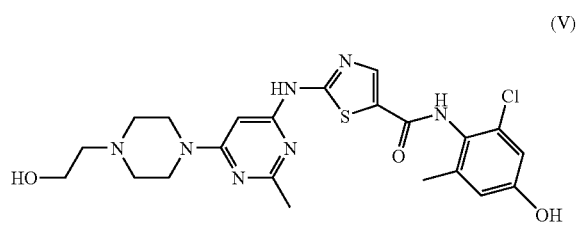

or a pharmaceutically acceptable salt form thereof.

5. A substantially pure compound of formula (VI),

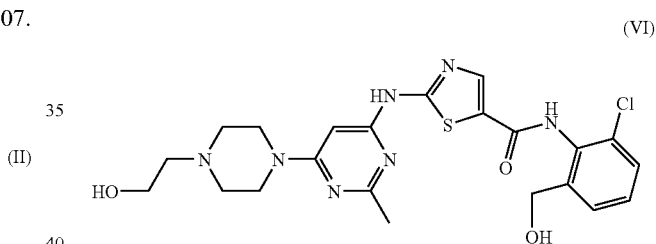

or a pharmaceutically acceptable salt form thereof.

6. A pharmaceutical composition, comprising a pharmaceutically acceptable vehicle or diluent and the compound of claim 1.

7. A pharmaceutical composition, comprising a pharmaceutically acceptable vehicle or diluent and the compound of claim 2.

8. A pharmaceutical composition, comprising a pharmaceutically acceptable vehicle or diluent and the compound of claim 3.

9. A pharmaceutical composition, comprising a pharmaceutically acceptable vehicle or diluent and the compound of claim 4.

10. A pharmaceutical composition, comprising a pharmaceutically acceptable vehicle or diluent and the compound of claim 5.

* * * * *

UNITED STATES PATENT AND TRADEMARK OFFICE
CERTIFICATE OF CORRECTION

| | | |
|---|---|---|
| PATENT NO. | : 7,622,473 B2 | Page 1 of 1 |
| APPLICATION NO. | : 11/376665 | |
| DATED | : November 24, 2009 | |
| INVENTOR(S) | : Vinod Kumar Arora et al. | |

It is certified that error appears in the above-identified patent and that said Letters Patent is hereby corrected as shown below:

Column 11, line 55, change "formula (II)" to -- formula (III) --.

Column 12, line 28, change "M 15" to -- M15 --.

Signed and Sealed this
Twentieth Day of December, 2011

David J. Kappos
*Director of the United States Patent and Trademark Office*